United States Patent
Ripberger et al.

(10) Patent No.: US 11,147,268 B2
(45) Date of Patent: Oct. 19, 2021

(54) FOOD CONTACT SURFACE SANITIZING LIQUID

(71) Applicant: THE CLOROX COMPANY, Oakland, CA (US)

(72) Inventors: Carrie Ripberger, Pleasanton, CA (US); Julie Timberman, Pleasanton, CA (US); William McCormick, III, Pleasanton, CA (US); Phoebe Leppla, Pleasanton, CA (US); Samuel Garber, Pleasanton, CA (US)

(73) Assignee: THE CLOROX COMPANY, Oakland, CA (US)

( * ) Notice: Subject to any disclaimer, the term of this patent is extended or adjusted under 35 U.S.C. 154(b) by 0 days.

(21) Appl. No.: 15/351,257

(22) Filed: Nov. 14, 2016

(65) Prior Publication Data
US 2017/0164612 A1    Jun. 15, 2017

Related U.S. Application Data

(60) Provisional application No. 62/265,800, filed on Dec. 10, 2015.

(51) Int. Cl.
| | | |
|---|---|---|
| *A01N 33/12* | (2006.01) | |
| *A61L 2/18* | (2006.01) | |
| *C11D 3/00* | (2006.01) | |
| *C11D 3/43* | (2006.01) | |
| *C11D 1/835* | (2006.01) | |
| *C11D 3/50* | (2006.01) | |
| *C11D 17/00* | (2006.01) | |
| *C11D 3/48* | (2006.01) | |
| C11D 1/62 | (2006.01) | |
| C11D 1/72 | (2006.01) | |
| C11D 1/66 | (2006.01) | |

(52) U.S. Cl.
CPC ................ *A01N 33/12* (2013.01); *A61L 2/18* (2013.01); *C11D 1/835* (2013.01); *C11D 3/0026* (2013.01); *C11D 3/43* (2013.01); *C11D 3/48* (2013.01); *C11D 3/50* (2013.01); *C11D 17/0008* (2013.01); C11D 1/62 (2013.01); C11D 1/662 (2013.01); C11D 1/72 (2013.01)

(58) Field of Classification Search
CPC .......... A01N 33/12; A01N 25/02; C11D 1/62; C11D 1/662; C11D 1/72; C11D 1/835; C11D 3/0026; C11D 7/0008; C11D 3/43; C11D 3/48; C11D 3/50; A61L 12/18
See application file for complete search history.

(56) References Cited

U.S. PATENT DOCUMENTS

| | | | |
|---|---|---|---|
| 6,410,041 B1 * | 6/2002 | Lewis | ................ A61K 31/4375 424/405 |
| 6,689,223 B1 | 2/2004 | Meine et al. | |
| 6,767,881 B1 | 7/2004 | Griese et al. | |
| 6,821,940 B2 | 11/2004 | Bullock et al. | |
| 6,953,772 B2 | 10/2005 | Lopes | |
| 2006/0062832 A1 | 3/2006 | Lopes | |
| 2009/0197786 A1 | 8/2009 | Perry et al. | |
| 2009/0325855 A1 | 12/2009 | Gambogi et al. | |
| 2014/0171512 A1 | 6/2014 | Kloeppel et al. | |
| 2015/0265666 A1 * | 9/2015 | Modak | ................... A01N 65/00 424/616 |

FOREIGN PATENT DOCUMENTS

| | | |
|---|---|---|
| EP | 0934381 A1 | 8/1999 |
| WO | WO1997/18285 A1 | 5/1997 |
| WO | WO98/16605 A1 | 4/1998 |
| WO | 2007133934 A1 | 11/2007 |

OTHER PUBLICATIONS

Bhatia et al., Regulatory Toxicology and Pharmacology, 71 (2015), 52-62.*
G.M. Cramer et al., "Estimation of Toxic Hazard—A Decision Tree Approach"; Food and Cosmetics Toxicology, vol. 16 Issue 3 (1976); pp. 255-276, specifically p. 264 col. 1 para 3, appendix 1.
PCT International Search Report for PCT/US2016/62313, dated Feb. 14, 2017.
European Search Report for PCT/US2016062313; dated Jun. 11, 2019.
"Lysol Disinfecting Wipes," https://www.lysol.com/products/disinfecting-wipes/lysol-disinfecting-wipes, retrieved Aug. 19, 2021.
"Claire No Rinse Food Surface Sanitizing Wipes (10" × 6" 100 Wipe Canisters)—Case of 6," https://www.cleanfreak.com/chemicals/disinfectants/food-grade/claire-food-surface-sanitizing-wipes.html, retrieved Aug. 19, 2021.
"CL913 Technical Data Sheet," https://media3.cleanfreak.com/documents/literature/claire-cl913-sanitizing-wipes-technical-data-sheet.pdf, retrieved Aug. 19, 2021.

(Continued)

*Primary Examiner* — Genevieve S Alley
(74) *Attorney, Agent, or Firm* — Workman Nydegger

(57) ABSTRACT

The present invention is for sanitizing compositions for sanitizing surfaces which may contact food. The composition may be provided in liquid form, and may include a quaternary amine, one or more surfactant, a fragrance, and water. At least 90% by weight of the fragrance comprises fragrance components that meet Class I qualifications of the Cramer classification system. All other components of the composition (e.g., the quaternary amine, the surfactants, water, and any optional components) meet the EPA guidelines under CFR 180.940(a). Since the composition only includes components that meet the EPA guidelines under CFR 180.940(a) (reflecting a presumption of low toxicity), and at least 90% of the fragrance itself (e.g., in the case of mixtures of fragrance components) meets the Cramer Class I qualifications, the composition is safe for application to surfaces that come in contact with food, where there is a heightened probability that traces of the composition will be ingested.

15 Claims, 1 Drawing Sheet

(56) References Cited

OTHER PUBLICATIONS

"Sani Professional No-Rinse Sanitizing Multi-Surface Wipes," https://media3.cleanfreak.com/documents/literature/sani-professional-no-rinse-sanitizing-wipes-technical-data-bulletin.pdf, retrieved Aug. 19, 2021.

"Lysol Kitchen Pro Antibacterial Cleaner," https://www.walmart.com/ip/Lysol-Kitchen-Pro-Antibacterial-Kitchen-Cleaner-Spray-22oz-No-Harsh-Chemicals/11027232, retrieved Aug. 19, 2021.

"§180.940 Tolerance exemptions for active and inert ingredients for use in antimicrobial formulations (Food-contact surface sanitizing solutions)," https://www.ecfr.gov/cgi-bin/text-idx?SID=27f89c62f973a6a2d3f50861b7378b85&mc=true&node=se40.26.180_1940&rgn=div8, retrieved Aug. 19, 2021.

* cited by examiner

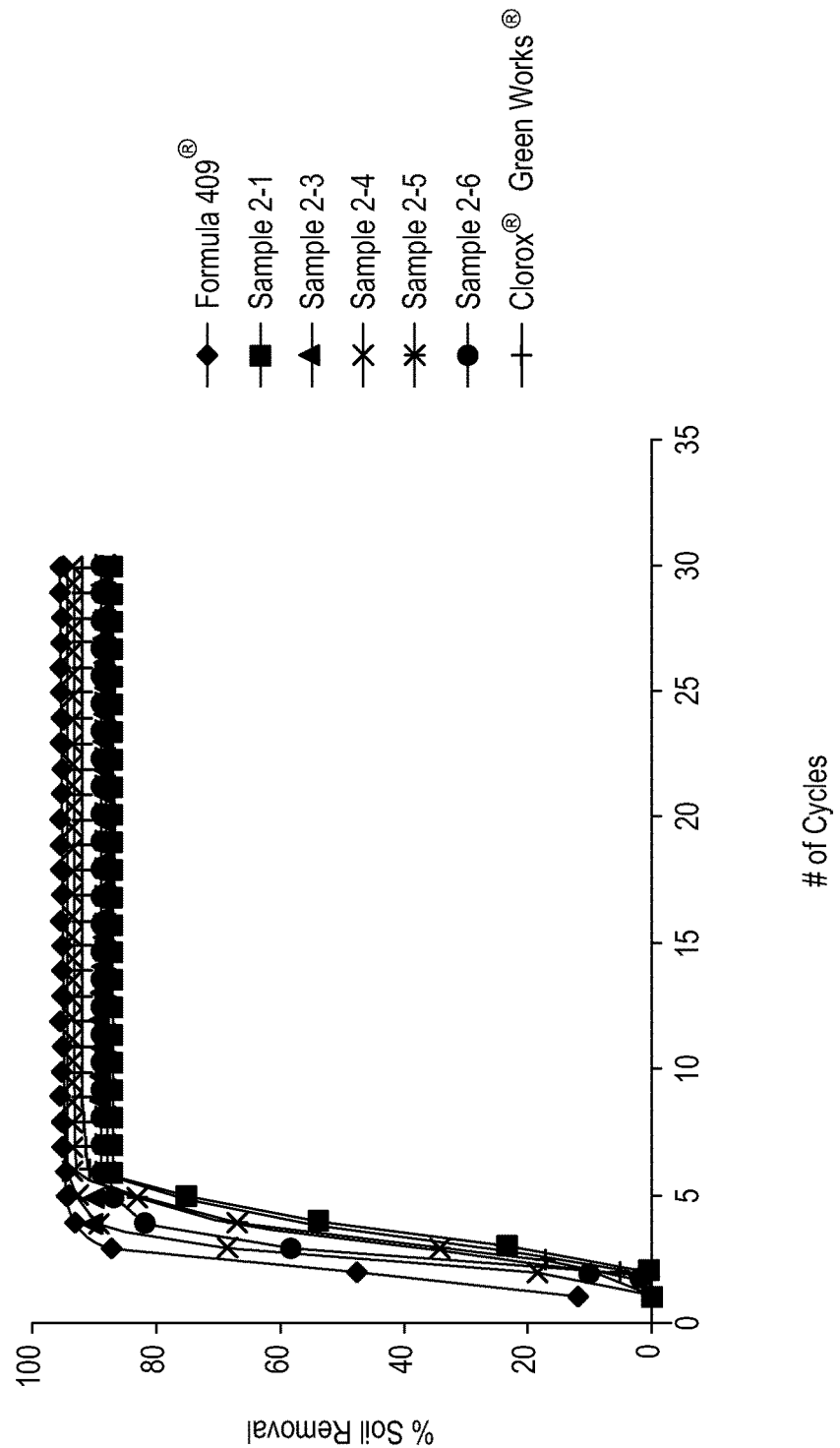

FOOD CONTACT SURFACE SANITIZING LIQUID

The present application claims the benefit of U.S. Provisional Patent Application Ser. No. 62/265,800, filed on Dec. 10, 2015, the disclosure of which is incorporated by reference in its entirety.

BACKGROUND OF THE INVENTION

1. The Field of the Invention

The present invention is generally related to compositions for use in sanitizing surfaces, particularly surfaces that are intended to come into contact with food (e.g., dishes, countertops, tables, utensils, etc.).

2. Description of Related Art

Various liquid compositions are available for use in sanitizing hard surfaces. Generally such compositions are effective in reducing microbial populations on such surfaces, although the use of many such existing compositions may be inappropriate for use on surfaces that are expected to come in contact with food. For example, when sanitizing food contact surfaces, it is desirable to limit the presence of components which may exhibit unwanted effects if inadvertently contacted with food, and possibly ingested. Similar considerations may apply to surfaces routinely handled by children, as they are more prone to put their hands in their mouths after touching or otherwise handling such a surface (e.g., toys, high-chairs, tables, cribs, etc.).

Balancing such a need to prevent or minimize inadvertent food contact and possible ingestion of components of the composition with the need for such compositions to be effective in killing microbes presents a challenge of competing requirements.

The present disclosure provides compositions generally recognized as safe for use in sanitizing food contact surfaces, while at the same time being effective in killing microbes present on such surfaces.

BRIEF SUMMARY OF THE INVENTION

In an embodiment, the present invention is directed to sanitizing compositions for sanitizing surfaces which may contact food. The composition may be provided in liquid form, and may include a quaternary amine, at least two non-ionic surfactants, a fragrance, and water. At least 90% of the fragrance comprises fragrance components that meet Class I qualifications of the Cramer classification system (e.g., as set forth in "Estimation of Toxic Hazard—A Decision Tree Approach", FOOD AND COSMETICS TOXICOLOGY, Vol. 16. pp. 255-276 (1978)). All other components of the composition (e.g., the quaternary amine, the surfactants, water, and any optional components) meet EPA guidelines under CFR 180.940(a). The Cramer classification system referenced above is herein incorporated by reference in its entirety.

Because other than the fragrance, the composition only includes components that meet the EPA guidelines under CFR 180.940(a) (reflecting a presumption of low toxicity), and at least 90% of the fragrance itself (e.g., in the case of mixtures of fragrance components) meets the Cramer Class I qualifications, the composition is safe for application to surfaces that come in contact with food, where there is a heightened probability that traces of the composition will be ingested. This heightened probability of ingestion is particularly applicable to babies and children. For example, the compositions may be particularly beneficial in sanitizing and cleaning a tray of a high-chair, in cleaning countertops, tabletops, dishes, utensils, and other surfaces which typically come in contact with food. The compositions may similarly be beneficial in sanitizing children's toys, where there is an increased likelihood that the user will insert hands or fingers into their mouth after touching the toy surface.

The composition is able to provide a high level of sanitization (i.e., killing of microbes) to such surfaces because of the presence of the quaternary amine. The presence of the fragrance provides a particular benefit in that the sanitizing composition is thus scented or fragranced, which provides an important aesthetic benefit to end users, who would appreciate the fragranced characteristics of the composition over an otherwise similar composition, but which does not include a desirable fragrance. In other words, the composition may exhibit an aesthetically desirable scent or fragrance (used interchangeably herein), such as may be provided by one or more essential oils, or other fragrance component, rather than a "chemical" or "cleaner" odor associated with the combination of components included within such a composition for other purposes. In other words, rather than having the scent of a surfactant, an antimicrobial agent, or other chemical constituents that are included for purposes other than fragrance, the composition provides an aesthetically desirable scent thereto, by including a fragrance component which is included specifically for this purpose.

According to another embodiment of the present disclosure, a fragranced sanitizing liquid composition for sanitizing surfaces which may contact food may include a quaternary amine, a blend of at least two non-ionic surfactants (e.g., an alkyl polyglucoside and an alcohol ethoxylate), a fragrance, water, and if included, less than 0.5% of a $C_1$-$C_4$ alcohol (e.g., ethanol, isopropyl alcohol, etc.). At least 90% of the fragrance comprises fragrance components that meet Class I qualifications of the Cramer classification system. In addition to limiting content of any low molecular weight alcohol (e.g., a $C_1$-$C_4$ alcohol such as ethanol or isopropyl alcohol), the composition may be void of polybiguanides and include (if at all) less than 0.5% of compounds with a vapor pressure over 0.1 mm Hg at 20° C. (other than water).

Another aspect of the present disclosure relates to a method of sanitizing a food contact surface including contacting a food contact surface with a sanitizing liquid composition such as any of those disclosed herein.

Further features and advantages of the present invention will become apparent to those of ordinary skill in the art in view of the detailed description of preferred embodiments below.

BRIEF DESCRIPTION OF THE DRAWINGS

To further clarify the above and other advantages and features of the present invention, a more particular description of the invention will be rendered by reference to specific embodiments thereof which are illustrated in the drawings located in the specification. It is appreciated that these drawings depict only typical embodiments of the invention and are therefore not to be considered limiting of its scope. The invention will be described and explained with additional specificity and detail through the use of the accompanying drawings in which:

FIG. 1 plots percent soil removal versus number of cycles for various sanitizing compositions according to the present invention, and for various comparative compositions.

DETAILED DESCRIPTION OF THE PREFERRED EMBODIMENTS

I. Definitions

Before describing the present invention in detail, it is to be understood that this invention is not limited to particularly exemplified compositions, systems or process parameters that may, of course, vary. It is also to be understood that the terminology used herein is for the purpose of describing particular embodiments of the invention only, and is not intended to limit the scope of the invention in any manner.

All publications, patents and patent applications cited herein, whether supra or infra, are hereby incorporated by reference in their entirety to the same extent as if each individual publication, patent or patent application was specifically and individually indicated to be incorporated by reference.

The term "comprising" which is synonymous with "including," "containing," or "characterized by," is inclusive or open-ended and does not exclude additional, unrecited elements or method steps.

The term "consisting essentially of" limits the scope of a claim to the specified materials or steps "and those that do not materially affect the basic and novel characteristic(s)" of the claimed invention.

The term "consisting of" as used herein, excludes any element, step, or ingredient not specified in the claim.

It must be noted that, as used in this specification and the appended claims, the singular forms "a," "an" and "the" include plural referents unless the content clearly dictates otherwise. Thus, for example, reference to a "surfactant" includes one, two or more surfactants.

The compositions described herein may provide sanitization, disinfection, or sterilization. As used herein, the term "sanitize" shall mean the reduction of contaminants in the inanimate environment to levels considered safe according to public health ordinance, or that reduces the bacterial population by significant numbers where public health requirements have not been established. By way of example, an at least 99% reduction in bacterial population within a 24 hour time period is deemed "significant." Greater levels of reduction are possible, as are faster treatment times (e.g., within 1 minute), when sanitizing. As used herein, the term "disinfect" shall mean the elimination of many or all pathogenic microorganisms on surfaces with the exception of bacterial endospores. As used herein, the term "sterilize" shall mean the complete elimination or destruction of all forms of microbial life and which is authorized under the applicable regulatory laws to make legal claims as a "sterilant" or to have sterilizing properties or qualities. Some embodiments of the present compositions provide for at least a 3 or more log reduction in bacterial population within a designated time period. A 3-log reduction is equivalent to at least a 99.9% reduction, a 4-log reduction is equivalent to at least a 99.99% reduction, a 5-log reduction is equivalent to at least a 99.999% reduction, etc.

The term "food contact surface" means as defined by the EPA and/or FDA. For example, the FDA defines the term in its "Food Code" 1-201.10 as (1) a surface of equipment or a utensil with which food normally comes into contact; or (2) a surface of equipment or a utensil from which food may drain, drip, or splash (a) into a food, or (b) onto a surface normally in contact with food.

Numbers, percentages, ratios, or other values stated herein may include that value, and also other values that are about or approximately the stated value, as would be appreciated by one of ordinary skill in the art. A stated value should therefore be interpreted broadly enough to encompass values that are at least close enough to the stated value to perform a desired function or achieve a desired result, and/or values that round to the stated value. The stated values include at least the variation to be expected in a typical manufacturing or formulation process, and may include values that are within 25%, within 20%, within 10%, within 5%, within 1%, etc. of a stated value. Furthermore, the terms "substantially", "similarly", "about" or "approximately" as used herein represent an amount or state close to the stated amount or state that still performs a desired function or achieves a desired result. For example, the term "substantially" "about" or "approximately" may refer to an amount that is within 25%, within 20%, within 10% of, within 5% of, or within 1% of, a stated amount or value.

Some ranges may be disclosed herein. Additional ranges may be defined between any values disclosed herein as being exemplary of a particular parameter. All such ranges are contemplated and within the scope of the present disclosure.

In the application, effective amounts are generally those amounts listed as the ranges or levels of ingredients in the descriptions, which follow hereto. Unless otherwise stated, amounts listed in percentage ("%'s") are in weight percent (based on 100% active) of the sanitizing composition alone, not accounting for any substrate weight.

As used herein, the term "substrate" is intended to include any material that is used to clean an article or a surface. Examples of cleaning substrates include, but are not limited to nonwovens, sponges films and similar materials, which can be attached to a cleaning implement.

As used herein, the terms "nonwoven" or "nonwoven web" means a web having a structure of individual fibers or threads which are interlaid, but not in an identifiable manner as in a knitted web. Nonwoven webs may be formed from many processes, such as, for example, meltblowing processes, spunbonding processes, and bonded carded web processes.

As used herein, "disposable" is used in its ordinary sense to mean an article that is disposed or discarded after a limited number of usage events, preferably less than 25, more preferably less than 10, and most preferably after a single entire usage event.

As used herein, "wiping" refers to any shearing action that a substrate undergoes while in contact with a target surface. This includes hand or body motion, substrate-implement motion over a surface, or any perturbation of the substrate via energy sources such as ultrasound, mechanical vibration, electromagnetism, and so forth.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

II. Introduction

The present invention is directed to compositions with relatively low concentrations of active ingredients, which compositions provide for sanitization with no rinse application on food contact surfaces, e.g., per EPA regulations. The composition may advantageously include one or more fragrance components. Various components may be provided within the composition to solubilize the fragrance, and to sanitize. Such a composition may include a quaternary amine, first and/or second nonionic surfactant(s), isopropyl alcohol, a pH adjuster, fragrance, and water (e.g., deionized water). Because the concentration of ingredients other than water is so low, the water may comprise at least 90%, at least 95%, at least 96%, at least 97%, or at least 98% by weight of the composition.

The one or more fragrance components may be selected from a compilation of acceptable flavor industry components, which meet the least toxicologically hazardous (i.e., Class I status in the Cramer classification system) classification. The other individual components of the composition (e.g., surfactants, quaternary amine, etc.) may all meet Class I standards as well. Any fragrance components may also meet Class I standards. In the case of a fragrance that is a mixture (e.g., mixtures of essential oils), at least 90% of the components of the fragrance mixture meet Class I standards.

Further aspects of at least some embodiments of the composition include (i) the composition does not include biguanides (e.g., polybiguanide), which is often present in other products in order to achieve a desired level of sanitization; (ii) the composition contains, other than water, less than 0.5% of components (e.g., volatile organic compounds (VOCs)) with a vapor pressure over 0.1 mm Hg at 20° C.; (iii) the composition includes minimal (if any) organic or inorganic acids (e.g., used only for pH adjustment—not sanitization), allowing for better surface safety and lower residue (e.g., filming and streaking) characteristics; and/or (iv) the composition may include a particular surfactant ratio (e.g., first surfactant to second surfactant weight fraction ratio) for optimal solubilization of the fragrance and excellent low residue performance. Each of the above aspects are unusual of sanitizing compositions. For example, often existing sanitizing compositions provide sanitization through inclusion of biguanides, high fractions of volatile components, and/or high fractions of organic or other acids.

The compositions may be of relatively low viscosity—e.g., less than 10,000 centipoise, less than 5,000 centipoise, less than 1,000 centipoise, less than 100 centipoise, or less than 10 centipoise. Such "thin" aqueous liquids may be particularly suitable for use in sanitizing via spray or pump. The compositions may also be applied to a substrate. Of course, thicker, more viscous compositions (e.g., for use as a lotion) may also be possible.

III. Exemplary Compositions

A. Surfactants

The compositions may include a one or more surfactants, preferably two or more nonionic surfactants. In an embodiment, the composition includes an alkyl polyglucoside surfactant and an alcohol ethoxylate surfactant, both of which are nonionic. The alkyl polyglucoside has been found to provide for excellent film/streak performance with respect to minimizing any residue left behind on the surface to which the composition is applied. The alcohol ethoxylate has been found to provide for excellent solubility of the fragrance, which typically exhibits hydrophobic characteristics, within the aqueous composition. The combination of the alkyl polyglucoside and the alcohol ethoxylate thus allows for a single phase, stable composition that is not hazy or cloudy, even after prolonged storage (e.g., after 1 day, after 1 week, after 1 month, after 6 months, after 1 year, etc.). The essential oil or other fragrance is solubilized in the water carrier (e.g., by the one or more surfactants), while exhibiting little or no filming and/or streaking (i.e., the composition exhibits low residue performance).

Various alkyl polyglucoside surfactants are suitable for use. Particularly preferred suitable non-ionic low residue surfactants are the alkyl polysaccharides that are disclosed in U.S. Pat. No. 5,776,872 to Giret et al.; U.S. Pat. No. 5,883,059 to Furman et al.; U.S. Pat. No. 5,883,062 to Addison et al.; and U.S. Pat. No. 5,906,973 to Ouzounis et al. Suitable alkyl polyglucosides for use herein are also disclosed in U.S. Pat. No. 4,565,647 to Llenado describing alkyl polyglucosides having a hydrophobic group containing from 6 to 30 carbon atoms, or from 10 to 16 carbon atoms and polysaccharide, e.g., a polyglycoside hydrophilic group containing from 1.3 to 10, or from 1.3 to 3, or from 1.3 to 2.7 saccharide units. Optionally, there can be a polyalkyleneoxide chain joining the hydrophobic moiety and the polysaccharide moiety. A suitable alkyleneoxide is ethylene oxide. Typical hydrophobic groups include alkyl groups, either saturated or unsaturated, branched or unbranched containing from 8 to 18, or from 10 to 16 carbon atoms. Suitably, the alkyl group can contain up to 3 hydroxy groups and/or the polyalkyleneoxide chain can contain up to 10, or less than 5, alkyleneoxide moieties. Suitable alkyl polysaccharides are octyl, nonyldecyl, undecyldodecyl, tridecyl, tetradecyl, pentadecyl, hexadecyl, heptadecyl, and octadecyl, di-, tri-, tetra-, penta-, and hexaglucosides, galactosides, lactosides, glucoses, fructosides, fructoses and/or galactoses. Suitable mixtures include coconut alkyl, di-, tri-, tetra-, and pentaglucosides and tallow alkyl tetra-, penta-, and hexaglucosides.

Suitable alkyl polyglycosides (or alkyl polyglucosides) have the formula:

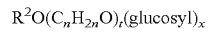

$$R^2O(C_nH_{2n}O)_t(\text{glucosyl})_x$$

wherein $R^2$ is selected from the group consisting of alkyl, alkyl phenyl, hydroxyalkyl, hydroxyalkylphenyl, and mixtures thereof in which the alkyl groups contain from 8 to 18, preferably from 8 to 14 carbon atoms, more preferably from 8 to 12 carbon atoms; n is 2 or 3, preferably 2; t is from 0 to 10, preferably 0; and x is from 1.3 to 10, preferably from 1.3 to 3, most preferably from 1.3 to 2.7. The glycosyl is preferably derived from glucose. To prepare these compounds, the alcohol or alkyl polyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominantly the 2-position.

A group of alkyl glycoside surfactants suitable for use in the practice of this invention may be represented by Formula I below:

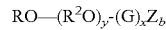

$$RO\text{—}(R^2O)_y\text{-}(G)_xZ_b \qquad \text{Formula I}$$

wherein R is a monovalent organic radical containing from 6 to 30 (preferably from 8 to 18) carbon atoms; $R^2$ is a divalent hydrocarbon radical containing from 2 to 4 carbon atoms; 0 is an oxygen atom; y is a number which has an average value from 0 to 1 and is preferably 0; G is a moiety derived from a reducing saccharide containing 5 or 6 carbon atoms; and x is a number having an average value from about 1 to 5 (preferably from 1.1 to 2); Z is $O_2M^1$, $O_2CR^3$, $O(CH_2)$, $CO_2M^1$, $OSO_3M^1$, or $O(CH_2)SO_3M^1$; $R^3$ is $(CH_2)$ $CO_2M^1$ or $CH\!=\!CHCO_2M^1$; (with the proviso that Z can be $O_2M^1$ only if Z is in place of a primary hydroxyl group in which the primary hydroxyl-bearing carbon atom, —$CH_2OH$, is oxidized to form a —$CO_2M^1$ group); b is a number from 0 to 3x+1 preferably an average of from 0.5 to 2 per glycosal group; p is 1 to 10, $M^1$ is $H^+$ or an organic or inorganic cation, such as, for example, an alkali metal, ammonium, monoethanolamine, or calcium. As defined in Formula I, R is generally the residue of a fatty alcohol having from 8 to 30 or 8 to 18 carbon atoms. Suitable alkylglycosides include, for example, Glucopon® 215 UP (a $C_8$-$C_{10}$ alkyl polyglucoside available from Cognis Corporation), APG 325® (a $C_9$-$C_{11}$ alkyl polyglycoside available from Cognis Corporation), APG 625® (a $C_{10}$-$C_{16}$ alkyl polyglycoside available from Cognis Corporation), Dow Triton® CG110 (a $C_8$-$C_{10}$ alkyl polyglycoside available from Dow Chemical Company), AG6202® (a $C_8$ alkyl polyglycoside available from Akzo Nobel) Alkadet 150 (a $C_8$-$C_{10}$ alkyl polyglycoside available from Huntsman Corporation), and Glucopon® 420 UP (available from BASF). A $C_8$ to $C_{10}$ alkyl polyglucoside includes alkyl polyglucosides wherein the alkyl group is substantially $C_8$ alkyl, substantially $C_{10}$ alkyl, or a mixture of substantially $C_8$ and $C_{10}$ alkyl. The $C_8$ to $C_{10}$ alkyl polyglucoside typically contains substantially no $C_9$ alkyl groups. The alkyl polyglycoside may be present in the liquid sanitizing composition in an amount ranging from 0 to 5 weight percent, 0.01 to 5.0 weight percent, 0.1 to 4.0 weight percent, 0.1 to 3.0 weight percent, 0.1 to 2.0 weight percent, 0.1 to 1.0 weight percent, 0.2 to 1 weight percent, or 0.3 to 1 weight percent, 0.2 to 0.5 weight percent, 0.2 to 1.55 weight percent, 0.4 to 1.55 weight percent, 0.6 to 1.55 weight percent, 0.8 to 1.55 weight percent, at least 0.1 weight percent, at least 0.2 weight percent, at least 0.3 weight percent, at least 0.4 weight percent, at least 0.5 weight percent, at least 0.6 weight percent, or at least 0.8 weight percent. 0.8 weight percent to 1.55 weight percent may be an appropriate amount to provide both good cleaning and low residue characteristics.

Exemplary alcohol ethoxylates include Ecosurf® EH9, and Ecosurf® EH6, available from Dow. Characteristics of EH9 and EH6 are shown in the table below.

| Characteristic | EH9 | EH6 |
|---|---|---|
| Cloud Point | 64[1] | 43[2] |
| HLB[3] | 12.5 | 10.8 |
| Moles EO | Proprietary | Proprietary |
| Pour Point | 16° C. | 5° C. |
| Appearance | Pale yellow liquid | Pale yellow liquid |
| pH, 1% aq. Solution | 6.2 | 6.2 |
| Viscosity @ 40° C., cSt | 49.40 | 36.83 |
| Density @ 40° C., g/mL | 1.0069 | 0.9897 |
| Flash Pt, Closed Cup, ASTM D93 | 288° C. | 263° C. |
| Critical Micelle Concentration @ 25° C. | 1066 ppm | 914 ppm |
| Surface Tension[4] | 31 | 30 |

[1]Cloud point: ° C., 10 wt % actives aqueous solution
[2]Cloud point: ° C., 10 wt % actives aqueous solution in 25:75 Butyl Carbitol:Water
[3]HLB Range: <10 w/o emulsifier, >10 o/w emulsifier, 10-15 good wetting, 12-15 detergents
[4]dynes/cm @ 1% actives, 25° C.

Alcohol ethoxylate surfactants may be made by reaction of a primary or secondary alcohol (e.g., $C_6$ to $C_{22}$, or $C_{12}$ to $C_{18}$) with ethylene oxide ($C_2H_4O$). Often the number of moles of ethoxylation is proprietary to the surfactant manufacturer (such as in EH9 and EH6, above). Additional examples of alcohol ethoxylate surfactants include Biosoft 91-6, available from Stepan, and other alcohol ethoxylates available from Dow under the tradename ECOSURF®. In one embodiment of the invention, the only surfactant in the composition is the alcohol ethoxylate. In this embodiment, the composition is essentially free of any other surfactants other than the alcohol ethoxylate. In an alternative embodiment, the alcohol ethoxylate may be combined with another surfactant (e.g. alkyl polyglucoside). The alcohol ethoxylate may be present in the liquid sanitizing composition in an amount ranging from 0.01 to 5 weight percent, 0.1 to 5.0 weight percent, 0.1 to 4.0 weight percent, 0.1 to 3.0 weight percent, 0.1 to 2.0 weight percent, 0.1 to 1.0 weight percent, 0.2 to 1 weight percent, or 0.3 to 1 weight percent, 0.2 to 0.5 weight percent, 0.4 to 1 weight percent, 0.5 to 1 weight percent, at least 0.05 weight percent, at least 0.1 weight percent, at least 0.15 weight percent, at least 0.2 weight percent, no more than 1 weight percent, no more than 0.8 weight percent, no more than 0.5 weight percent, no more than 0.4 weight percent, or no more than 0.3 weight percent. For example, 0.2 weight percent may be an appropriate amount for solubilization.

In one embodiment, total surfactant concentration of the two non-ionic surfactants (e.g., the alkyl polyglucoside to the alcohol ethoxylate) may be no more than, or less than 4%, no more than, or less than 3%, no more than, or less than 2.5%, no more than, or less than 2%, or no more than, or less than 1%. Various other concentration ranges may be derived from the examples.

In the embodiment of the invention with both alkyl polyglucoside and alcohol ethoxylate surfactants there are a range of suitable weight ratios of the two surfactants. In this embodiment, the weight ratio of the alkyl polyglucoside to the alcohol ethoxylate may be at least 1:1, greater than 1:1, at least 1.5:1, at least 2:1, at least 2.5:1, at least 3:1, at least 4:1, at least 5:1, at least 6:1, at least 7:1, at least 8:1, at least 9:1, at least 10:1, at least 12:1, at least 15:1, or at least 20:1. The ratio may range between any of the forgoing ratios (e.g., from 1:1 to 10:1, from 1:1 to 5:1, etc.). Various other ratios may be derived from the examples, which may be employed in ranges.

In some embodiments, the composition may contain one or more additional surfactants in addition to the blend of two nonionic surfactants (e.g., the alkyl polyglucoside and the alcohol ethoxylate). Such additional surfactants may be selected from anionic, cationic, ampholytic, amphoteric and zwitterionic surfactants and mixtures thereof. A typical listing of anionic, ampholytic, and zwitterionic classes, and species of these surfactants, is given in U.S. Pat. No. 3,929,678 to Laughlin and Heuring. A list of suitable cationic surfactants is given in U.S. Pat. No. 4,259,217 to Murphy. Where present, anionic, ampholytic, amphotenic and zwitteronic surfactants are generally used in combination with one or more (preferably two) nonionic surfactants. Where additional surfactants are included, they may be present at a concentration from greater than 0% to 50%, from 0.001% to 10%, from 0.1% to 2% by weight, or any of the ranges disclosed relative to the concentration of the alkyl polyglucoside or the alcohol ethoxylate surfactants.

Additional nonionic surfactants can be found in U.S. Pat. No. 3,929,678 to Laughlin et al. Essentially any alkoxylated nonionic surfactants are suitable herein, for instance, ethoxylated and propoxylated nonionic surfactants. Alkoxylated surfactants can be selected from the classes of the nonionic condensates of alkyl phenols, nonionic ethoxylated alcohols, nonionic ethoxylated/propoxylated fatty alcohols, nonionic ethoxylate/propoxylate condensates with propylene glycol, and the nonionic ethoxylate condensation products with propylene oxide/ethylene diamine adducts. Various alkyl polyethylene glycol ethers (e.g., made from a $C_{10}$ Guerbet alcohol and an alkylene oxide) may also be suitable for use. Examples of such alkyl polyethylene glycol ether surfactants include XL70 and XL90, available from BASF. Suitable anionic surfactants include salts (including, for example, sodium, potassium, ammonium, and substituted ammonium salts such as mono-, di- and tri-ethanolamine salts) of the anionic sulfate, sulfonate, carboxylate and sarcosinate surfactants.

Anionic surfactants may comprise a sulfonate or a sulfate surfactant. Anionic surfactants may comprise an alkyl sulfate, a linear or branched alkyl benzene sulfonate, or an alkyldiphenyloxide disulfonate, as described herein. Suitable amphoteric surfactants include the amine oxide surfactants and the alkyl amphocarboxylic acids. Suitable amine oxides include those compounds having the formula $R^3(OR^4)_xNO(R^5)_2$ wherein $R^3$ is selected from an alkyl, hydroxyalkyl, acylamidopropyl and alkylphenyl group, or mixtures thereof, containing from 8 to 26 carbon atoms; $R^4$ is an alkylene or hydroxyalkylene group containing from 2 to 3 carbon atoms, or mixtures thereof, x is from 0 to 5, preferably from 0 to 3; and each $R^5$ is an alkyl or hydroxyalkyl group containing from 1 to 3, or a polyethylene oxide group containing from 1 to 3 ethylene oxide groups. Suitable amine oxides are $C_{10}$-$C_{18}$ alkyl dimethylamine oxide, and $C_{10}$-$C_{18}$ acylamido alkyl dimethylamine oxide.

A suitable example of an alkyl amphodicarboxylic acid is Miranol® C2M Conc. Suitable zwitterionic surfactants include betaines having the formula $R(R^1)_2N^+R^2COO^-$ wherein R is a $C_6$-$C_{18}$ hydrocarbyl group, each $R^1$ is typically $C_1$-$C_3$ alkyl, and $R^2$ is a $C_1$-$C_5$ hydrocarbyl group. Suitable betaines are $C_{12}$-$C_{18}$ dimethyl-ammonio hexanoate and the $C_{10}$-$C_{18}$ acylamidopropane (or ethane) dimethyl (or diethyl) betaines.

Cationic surfactants may include the quaternary ammonium surfactants. The quaternary ammonium surfactant may be a mono $C_6$-$C_{16}$, or a $C_6$-$C_{10}$ N-alkyl or alkenyl ammonium surfactant wherein the remaining N positions are substituted by methyl, hydroxyethyl or hydroxypropyl groups. The mono-alkoxylated and bis-alkoxylated amine surfactants may also be suitable.

In at least some embodiments, as the composition already includes a quaternary amine anti-microbial component, which quaternary amines are cationic, the composition may not include anionic surfactants, as their presence may interfere with the effectiveness of the quaternary amine. In an embodiment, all surfactants included within the composition are non-ionic or cationic. In another embodiment, all surfactants included in the composition are non-ionic. Furthermore, although the included quaternary amine may exhibit some surface active characteristics, its inclusion in the composition is for anti-microbial purposes, not primarily for surfactant purposes. For example, the quaternary amine may be present at a level of 400 ppm (0.04%) or less by weight of the composition (e.g. 100 to 400 ppm). Where quaternary amines are included as surfactants in compositions, their concentration is typically significantly higher.

B. Quaternary Amine Antimicrobial Compounds

Sanitizing efficacy is provided by a quaternary amine included within the sanitizing compositions. As described above, the concentration of such a quaternary amine may typically be at a level of 400 ppm or less (e.g., 400 ppm, 300 ppm, 200 ppm, 100 ppm, or 50 ppm).

A wide range of quaternary amine compounds can be used as antimicrobial actives. Non-limiting exemplary quaternary compounds include: (1) benzalkonium chlorides and/or substituted benzalkonium chlorides such as commercially available BTC® (available from Stepan), Barquat® (available from Lonza), Maquat® (available from Mason), Variquat® (available from Witco/Sherex), and Hyamine® (available from Lonza); (2) di($C_6$-$C_{14}$)alkyl di short chain ($C_1$-$C_4$ alkyl and/or hydroxyalkyl) quaternary compounds such as Bardac® products of Lonza; (3) N-(3-chloroallyl)hexaammonium chlorides such as Dowicide® and Dowicil® available from Dow; (4) benzethonium chloride such as Hyamine® from Rohm & Haas; (5) methylbenzethonium chloride represented by Hyamine® 10× supplied by Rohm & Haas; (6) cetylpyridinium chloride such as cepacol chloride available from of Merrell Labs.

Exemplary dialkyl quaternary compounds are di($C_8$-$C_{12}$) dialkyl dimethyl ammonium chloride, such as didecyldimethyl-ammonium chloride (BTC® 1210 or Bardac® 22), and dioctyldimethylammonium chloride (Bardac® 2050). In an embodiment, the quaternary amine may be selected from the group consisting of dialkyldimethylammonium chlorides, alkyldimethylbenzylammonium chlorides, dialkylmethylbenzylammonium chlorides, diisobutylphenoxyethoxyethyl dimethylbenzylammonium chloride (commercially available under the trade name Hyamine® 1622 from Rohm & Haas) and (methyl) diisobutylphenoxyethoxyethyl dimethylbenzylammonium chloride (i.e. methylbenzethonium chloride). A suitable quaternary amine is BTC 1210®, which is a mixture of n-alkyl dimethyl benzyl ammonium chloride and dodecyl dimethyl ammonium chloride, available from Stepan. Another quaternary amine is BTC 2125®, which is a mixture of n-alkyl dimethyl benzyl ammonium chloride and n-alkyl dimethyl ethyl benzyl ammonium chloride.

The quaternary amine may be present at a concentration of not more than 400 ppm (0.04%), at least 100 ppm (0.01%), at least 200 ppm (0.02%), or at least 300 ppm (0.03%), e.g., from 100 ppm (0.01%) to 400 ppm (0.04%), from 200 ppm (0.02%) to 400 ppm (0.04%), from 300 ppm (0.03%) to 400 ppm (0.04%), or at about 400 ppm. In an embodiment, the quaternary amine is not included with a biguanide (which is another antimicrobial), but the sanitizing effect is provided by the quaternary amine without any such biguanide.

C. Fragrance

The present compositions advantageously include a fragrance, providing a fragranced sanitizing liquid composition effective to sanitize food contact surfaces. As described herein, the fragrance may include only components that meet Class I qualifications of the Cramer classification system. Where the fragrance comprises a mixture of essential oils, at least 90% of the fragrance components (e.g., a mixture of essential oils), meet Class I qualifications of the Cramer classification system. As described herein, all other components included within the composition may also meet Class I qualifications of the Cramer classification system, so that the composition is safe for use in sanitizing surfaces which routinely come into contact with food (e.g., counter tops, high chairs, appliances, tables, utensils, food packaging and other surfaces where there may be incidental contact with food, or surfaces which a child may handle and then insert their hand into their mouth (e.g., toys).

A non-exhaustive list of exemplary suitable fragrance ingredients, e.g., also allowed for flavor use under applicable U.S. FDA and FEMA GRAS regulations (found in various sections of 21 CFR) is included below in Table 1. The listing in Table 1 below includes chemically-defined fragrance ingredients, as well as ingredients derived from botanical sources (a.k.a. "naturals"). The chemically-defined fragrance ingredients have been reviewed by the joint FAO/WHO Expert Committee on Food Additives (JECFA). Starting with a listing of 1075 materials, 838 were chemically-defined, allowing for direct classification via the Cramer classification system. The published JECFA monographs for these materials were reviewed and assigned as by JECFA. Of the 838 chemically-defined materials, 664 are classified in Class I of the Cramer classification system. 131 are classified in Class II of the Cramer classification system, and 43 are classified in Class III of the Cramer classification system.

220 of the 1058 materials are derived from botanical sources (e.g., orange oil, etc.). In order to classify these materials as to their Cramer classes, a constituent based approach was employed, wherein quantitative analytical information was collected on each "natural" material. Following collection of the analytical data, each constituent was assigned a Cramer class. Of the 220, 64 had constituent assignments where all constituents were Class I. Of the remaining 156 materials, 21 had constituent assignments where Class I accounted for at least 90%, (e.g., greater than 90%) of the assay, with the remainder being Class II constituents only. Of the remaining 135, 55 had constituent assignments where Class I accounted for at least 90% (e.g., greater than 90%) of the assay, with the remainder constituents being Class II or Class III. The remaining 80 materials had constituents where Class III accounted for greater than 90% of the assay.

The fragrance may be included in an amount from 0.01 to 5 weight percent, 0.1 to 5.0 weight percent, 0.1 to 4.0 weight percent, 0.1 to 3.0 weight percent, 0.1 to 2.0 weight percent, 0.1 to 1.0 weight percent, 0.2 to 1 weight percent, 0.3 to 1 weight percent, 0.2 to 0.5 weight percent, 0.4 to 1 weight percent, 0.5 to 1 weight percent, at least 0.05 weight percent, at least 0.1 weight percent, at least 0.2 weight percent, at least 0.3 weight percent, at least 0.4 weight percent, or at least 0.5 weight percent. The fragrance (e.g., typically hydrophobic) may be solubilized into the composition by the surfactant, which is particularly well achieved by a blend of an alcohol ethoxylate and a alkyl polyglucoside surfactant.

TABLE 1

Exemplary Fragrances

| CAS Number | Chemical Name | Other Name |
|---|---|---|
| *Aliphatic, linear alpha, beta-unstaurated aldehydes, acids, and related alcohols* | | |
| 3913-71-1 | 2-Decenal | 2-Decenal |
| 6728-26-3 | Hexen-2-al | 2-Hexenal, (2E)- |
| 111-79-5 | Methyl 2-nonenoate | 2-Nonenoic acid, methyl ester |
| 111-80-8 | Methyl 2-nonynoate | 2-Nonenoic acid, methyl ester |
| 111-12-6 | Methyl 2-octynoate | |
| *Aliphatic acyclic acetals* | | |
| 28069-74-1 | Acetaldehyde ethyl cis-3-hexenyl acetal | 3-Hexene, 1-(1-ethoxyethoxy)-, (3Z)- |
| 7492-66-2 | 1,1-diethoxy-3,7-dimethylocta-2,6-diene | 2,6-Octadiene, 1,1-diethoxy-3,7-dimethyl- |
| 10022-28-3 | Octanal dimethyl acetal | Octane, 1,1-dimethoxy- |
| *Aliphatic acyclic and alicyclic terpenoid tertiary alcohols and structurally related substances* | | |
| 151-05-3 | Alpha,alpha-Dimethylphenethyl acetate | Benzeneethanol, .alpha.,.alpha.-dimethyl-, acetate |
| 10094-34-5 | Alpha,alpha-Dimethylphenethyl butyrate | Butanoic acid, 1,1-dimethyl-2-phenylethyl ester |
| 78-70-6 | Linalool | 1,6-Octadien-3-ol, 3,7-dimethyl- |
| 115-95-7 | Linalyl acetate | 1,6-Octadien-3-ol, 3,7-dimethyl-, acetate |
| 7212-44-4 | Nerolidol (isomer unspecified) | 1,6,10-Dodecatrien-3-ol, 3,7,11-trimethyl- |
| 98-55-5 | Alpha-Terpineol | 3-Cyclohexene-a-methanol, .alpha.,.alpha.,4-trimethyl- |
| 8007-35-0 | Terpinyl acetate (Isomer mixture) | Terpineol, acetate |
| 78-69-3 | Tetrahydrolinalool | 3-Octanol, 3,7-dimethyl- |
| *Aliphatic acyclic diols, triols, and related agents* | | |
| 102-76-1 | (tri-)Acetin | 1,2,3-Propanetriol, triacetate |
| *Aliphatic and alicyclic hydrocarbons* | | |
| 87-44-5 | Beta-Caryophyllene | Bicyclo[7.2.0]undec-4-ene4,11,11-trimethyl-8-methylene-, (1R,4E,9S)- |
| 98-85-4 | p-Mentha-1,4-diene | 1,4-Cyclohexadiene, 1-methyl-4-(1-methylethyl)- |
| 80-56-8 | Alpha-Pinene | Bicyclo[3.1.1]hept-2-ene,2,6,6-trimethyl- |
| 127-91-3 | Beta-Pinene | Bicyclo[3.1.1]hept-2-ene, 2,6,6-trimethyl- |
| 586-62-9 | Terpinolene | Cyclohexene, 1-methyl-4-(1-methylethylidene)- |
| *Aliphatic and aromatic ethers* | | |
| 101-84-8 | Diphenyl ether | Benzene, 1,1'-oxybis- |
| 470-82-6 | Eucalyptol | 2-Oxabicyclo[2.2.2]octane, 1,3,3-trimethyl- |
| 104-98-8 | p-Methylanisole | Benzene, 1-methoxy-4-methyl- |
| 16409-43-1 | Tetrahydro-4-methyl-2-(2-methylpropen-1-yl)pyran | 2H-Pyran,tetrahydro-4-methyl-2-(2-methyl-1-propenyl)- |
| *Aliphatic branched-chain unsaturated alcohols, aldehydes, acids, and related esters* | | |
| 106-23-0 | Citronellal | 6-Octenal, 3,7-dimethyl- |
| 106-25-2 | Nerol | 2,6-Octadien-1-ol, 3,7-dimethyl-, (2Z)- |

TABLE 1-continued

Exemplary Fragrances

| CAS Number | Chemical Name | Other Name |
|---|---|---|
| Aliphatic di-and trienals and related alcohols, acids, and esters ||| 
| 3025-30-7 | Ethyl (2E,4Z)-2,4-decadienoate | 2,4-Decadienoic acid, ethyl ester, (2E,4Z)- |
| 557-48-2 | Nona-2-trans-6-cis-dienal | 2,6-Nonadienal, (2E,6Z)- |
| Aliphatic lactones ||| 
| 706-14-9 | gamma-Decalactone | 2(3H)-Furanone, 5-hexyldihydro- |
| 105-21-5 | gamma-Heptalactone | 2(3H)-Furanone, dihydro-5-propyl- |
| 695-06-7 | gamma-Hexalactone | (3H)-Furanone, 5-ethyldihydro- |
| 3301-94-8 | Hydroxynonanoic acid, delta lactone | |
| 710-04-3 | 5-Hydroxyundecanoic acid lactone | 2H-Pyran-2-one, 6-hexyltetrahydro- |
| 28645-51-4 | Oxacycloheptadec-10-ene-2-one | Oxacycloheptadec-10-en-2-one |
| 104-61-0 | gamma-Nonalactone | 2(3H)-Furanone, dihydro-5-pentyl- |
| 104-50-7 | gamma-Octalactone | 2(3H)-Furanone, 5-butyldihydro- |
| 106-02-5 | omega-Pentadecalactone | Oxacyclohexadecan-2-one |
| 104-67-6 | gamma-Undecalactone | 2(3H)-Furanone, 5-heptyldihydro- |
| Aliphatic secondary alcohols, ketones and related esters and acetals ||| 
| 81925-81-7 | 5-Methyl-2-hepten-4-one | |
| 110-93-0 | 6-Methyl-5-hepten-2-one | 5-Hepten-2-one, 6-methyl- |
| Allyl esters ||| 
| 123-68-2 | Ally hexanoate | Hexanoic acid, 2-propenyl ester |
| Alphatic primary alcohols, aldehydes, carboxylic acids, acetals and esters ||| 
| 105-53-3 | Diethyl malonate | Propanedioic acid, diethyl ester |
| 141-97-9 | Ethyl acetoacetate | Butanoic acid, 3-oxo-, ethyl ester |
| 105-95-3 | Ethylene brassylate | 1,4-Dioxacycloheptadecane-5,17-dione |
| 107-75-5 | Hydroxycitronellal | Octanal, 7-hydroxy-3,7-dimethyl- |
| 107-74-4 | Hydroxycitronellol | 1,7-Octanediol, 3,7-dimethyl- |
| 705-86-2 | delta-Decalactone | 2H-Pyran-2-one, tetrahydro-6-pentyl- |
| 77-93-0 | Triethyl citrate | 1,2,3-Propanetricarboxylic acid, 2-hydroxy-, triethyl ester |
| Anthranilate derivatives ||| 
| 134-20-3 | Methyl anthranilate | Benzoic acid, 2-amino-, methyl ester |
| 85-91-6 | Methyl N-methylanthranilate | Benzoic acid, 2-(methylamino)-, methyl ester |
| Aromatic hydrocarbons ||| 
| 99-87-6 | p-Cymene | Benzene, 1-methyl-4-(1-methylethyl)- |
| Aromatic substituted secondary alcohols, ketones, and related ester ||| 
| 98-86-2 | Acetophenone | Ethanone, 1-phenyl- |
| 122-00-9 | 4'-Methylacetophenone | Ethanone, 1(4-methylphenyl)- |
| 93-92-5 | alpha-Methylbenzyl acetate | Benzenemethanol, alpha.-methyl-, acetate |
| 98-85-1 | alpha-Methylbenzyl alcohol | Benzenemethanol, alpha.-methyl- |
| 93-08-3 | Methyl beta-naphthyl ketone | Ethanone, 1-(2-naphthalenyl)- |
| Benzyl derivatives ||| 
| 100-52-7 | Benzaldehyde | Benzaldehyde |
| 140-11-4 | Benzyl acetate | Acetic acid, phenylmethyl ester |
| 100-51-6 | Benzyl alcohol | Benzenemethanol |
| 103-37-7 | Benzyl butyrate | Butanoic acid, phenylmethyl ester |
| 103-28-6 | Benzyl isobutyrate | Propanoic acid, 2-methyl-, phenylmethyl ester |
| 122-63-4 | Benzyl propionate | Propanoic acid, phenylmethyl ester |
| 122-03-2 | Cuminaldehyde | Benzaldehyde, 4-(1-methylethyl)- |
| 93-89-0 | Ethyl benzoate | Benzoic acid, ethyl ester |
| 93-58-3 | Methyl benzoate | Benzoic acid, methyl ester |
| Carvone and structurally related substances ||| 
| 20777-49-5 | Dihydrocarvyl acetate | |
| Cinnamyl derivatives ||| 
| 104-55-2 | Cinnamaldehyde | 2 Propenal, 3-phenyl- |
| 104-54-1 | Cinnamyl alcohol | 2-Propen-1-ol, 3-phenyl- |
| 101-86-0 | alpha-Hexylcinnamaldehyde | Octanal, 2-(phenylmethylene)- |
| 101-39-3 | alpha-Methylcinnamaldehyde | 2-Propenal, 2-methyl-3-phenyl- |
| 103-26-4 | Methyl cinnamate | 2 Propenoic acid, 3-phenyl-, methyl ester |
| 122-97-4 | 3-Phenyl 1-propanol | Benzenepropanol |

TABLE 1-continued

Exemplary Fragrances

| CAS Number | Chemical Name | Other Name |
|---|---|---|
| Esters of aliphatic acyclic primary alcohols with aliphatic linear saturated carboxylic acids | | |
| 16491-36-4 | cis-3-Hexenyl butyrate | Butanoic acid, (3Z)-3-hexenyl ester |
| 31501-11-8 | cis-3-Hexenyl hexanoate | Hexanoic acid, (3Z)-3-hexenyl ester |
| 2639-63-6 | Hexyl butyrate | Butanoic acid, hexyl ester |
| 6378-65-0 | Hexyl hexanoate | Hexanoic acid, hexyl ester |
| 2445-76-3 | Hexyl propionate | |
| 110-19-0 | Ixobutyl acetate | |
| 112-19-6 | 10-Undecen-1-yl acetate | |
| Esters of aliphatic primary alcohols with branched-chain aliphatic acyclic acids | | |
| 97-62-1 | Ethyl isobutyrate | Propanoic acid, 2-methyl-, ethyl ester |
| 10094-41-4 | 3-Hexenyl 2-methylbutanoate | |
| 2349-07-7 | Hexyl isobutyrate | |
| 97-85-8 | Isobutyl isobutyrate | Propanoic acid, 2-methyl-, 2-methylpropyl ester |
| 66576-71-4 | Isopropyl 2-methylbutyrate | Butanoic acid, 2-methyl-, 1-methylethyl ester |
| Ethyl esters | | |
| 141-78-6 | Ethyl acetate | Acetic acid ethyl ester |
| 105-54-4 | Ethyl butyrate | Butanoic acid, ethyl ester |
| 110-38-3 | Ethyl decanoate | Decanoic acid, ethyl ester |
| 106-33-2 | Ethyl laurate | Dodecanoic acid, ethyl ester |
| 106-30-9 | Ethyl heptanoate | Heptanoic acid, ethyl ester |
| 123-66-0 | Ethyl hexanoate | Hexanoic acid, ethyl ester |
| 123-29-5 | Ethyl nonanoate | Nonanoic acid, ethyl ester |
| 106-32-1 | Ethyl octanoate | Octanoic acid, ethyl ester |
| Eugenol and related hydroxyallybenzene derivatives | | |
| 97-53-0 | Eugenol | Phenol, 2-methoxy-4-(2-propenyl)- |
| Hydroxy-and alkoxy-substituted benzyl derivatives | | |
| 118-61-6 | Ethyl salicylate | Benzoic acid, 2-hydroxy-, ethyl ester |
| 123-11-5 | p-Methoxybenzaldehyde | Benzaldehyde, 4-methoxy- |
| 119-36-8 | Methyl salicylate | Benzoic acid, 2-hydroxy-, methyl ester 121-33-5 |
| 121-33-5 | Vanillin | Benzaldehyde, 4-hydroxy-3-methoxy- |
| 20665-85-4 | Propanoic acid, 2-methyl-, 4-formyl-2-methoxyphenyl ester | |
| 120-14-9 | Veratraldehyde | Benzaldehyde, 3,4-dimethoxy- |
| Hydroxypropylbenzenes | | |
| 97-54-1 | Isoeugenol | Phenol, 2-methoxy-4-(1-propenyl)- |
| Ionones and structurally related substances | | |
| 79-78-7 | Allyl alpha-ionone | 1,6-Heptadien-3-one, 1-(2,6,6-trimethyl-2-cyclohexen-1-yl). |
| 23696-85-7 | 1-(2,6,6-Trimethylcyclohexa-1,3-dienyl)-2-buten-1-one | 2-Buten-1-one,1-(2,6,6-trimethyl-1,3-cyclohexadien-1-yl)- |
| 24720-09-0 | 2-Buten-1-one, 1-(2,6,6-trimethyl-2-cyclohexen-1-yl)-, (2E)- | 2-Buten-1-one, 1-(2,6,6-trimethyl-2-cyclohexadien-1-yl)-, (2E)- |
| 57378-68-4 | Delta-1-(2,6,6-Trimethyl-3-cyclohexen-1-yl)-2-buten-1-one | 2-Buten-1-one, 1-(2,6,6-trimethyl-3-cyclohexen-1-yl)- |
| 17283-81-7 | Dihydro-beta-ionone | 2-Butanone, 4-(2,6,6-trimethyl-1-cyclohexen-1-yl)- |
| 127-51-5 | alpha-iso-Methylionone | 3-Buten-2-one, 3-methyl-4-(2,6,6-trimethyl-2-cyclohexen-1-yl)- |
| Isoamyl alcohol & related esters | | |
| 123-92-2 | Isoamyl acetate | 1-Butanol, 3-methyl-, acetate |
| 123-51-3 | Isoamyl alcohol | 1-Butanol, 3-methyl- |
| 106-27-4 | Isoamyl butyrate | Butanoic acid, 3-methylbutyl ester |
| Linear and branched-chain aliphatic unsaturated non-conjugated alcohols, aldehydes | | |
| 35854-86-5 | cis-6-Nonen-1-ol | 6-Nonen-1-ol, (6Z)- |
| 2277-19-2 | cis-6-Nonenal | |
| Linear and branched-chain unsaturated, unconjugated alcohols, aldehydes, acids | | |
| 39770-05-3 | 9-Decenal | 9-Decenal |
| 41519-23-7 | cis-3-Hexenyl isobutyrate | Propanoic acid, 2-methyl-, (3Z)-3-hexenyl ester |
| Monocyclic and bicyclic secondary alcohols, ketones, and related esters | | |
| 5655-61-8 | laevo-Bornyl acetate | Bicyclo[2.2.1]heptan-2-ol, 1,7,7-trimethyl-, acetate, (1S,2R,4S)- |
| 1632-73-1 | Fenchyl alcohol | Bicyclo[2.2.1]heptan-2-ol, 1,3,3-trimethyl- |
| 124-76-5 | Isoborneol | Bicyclo[2.2.1]heptan-2-ol, 1,7,7-trimethyl-, (1R,2R,4R)-rel- |

TABLE 1-continued

Exemplary Fragrances

| CAS Number | Chemical Name | Other Name |
|---|---|---|
| 125-12-2 | Isobornyl acetate | Bicyclo[2.2.1]heptan-2-ol, 1,7,7-trimethyl-, acetate, (1R, 2R 4R)-rel- |
| 2756-56-1 | Isobornyl propionate | Bicyclo[2.2.1]heptan-2-ol, 1,7,7-trimethyl-, propanoate, (1R,2R,4R)-rel- |
| 13851-11-1 | 1,3,3-Trimethyl-2-norbornanyl acetate | Bicycio[2.2.1]heptan 2-ol, 1,3,3-trimethyl-, acetate |

Phenethyl alcohol, aldehyde, acid and related acetals and esters

| 103-45-7 | Phenethyl acetate | Acetic acid, 2-phenylethyl ester |
| 60-12-8 | Phenethyl alcohol | Benzeneethanol |
| 103-48-0 | Phenethyl isobutyrate | Propanoic acid, 2-methyl-, 2-phenylethyl ester |
| 102-20-5 | Phenethyl phenylacetate | Benzeneacetic acid, 2-phenylethyl ester |
| 101-48-4 | Phenylacetaldehyde dimethyl acetal | Benzene, (2,2-dimethoxyethyl)- |

Phenol and phenol derivatives

| 499-75-2 | Carvacrol | Phenol, 2-methyl-5-(1-rnethylethyl)- |
| 5471-51-2 | 4-(p-Hydroxyphenyl)-2-butanone | 2-Butanone, 4-(4-hydroxyphenyl)- |
| 2785-87-7 | 2-Methoxy-4-propylphenol | Phenol, 2-methoxy-4-propyl- |
| 89-83-8 | Thymol | Phenol, 5-methyl-2-(1-rnethylethyl)- |

Phenylsubstituted aliphatic alcohols and related aldehydes and esters

| 103-95-7 | 2-Methyl-3-(p-isopropylphenyl)propionaldehyde | Benzenepropanal, .alpha.-methyl-4-(1-methylethyl)- |
| 103-05-9 | 2-Methyl-4-phenyl-2-butanol | Benzenepropanol, .alpha.,.alpha.-dimethyl- |
| 93-53-8 | 2-Phenylpropionaldehyde | Benzeneacetaldehyde, .alpha.-methyl- |
| 90-87-9 | 2-Phenylpropionaldehyde dimethyl acetal | Benzene, (2,2-dimethoxy-1-methylethyl)- |

Pyridine, pyrrole and quinoline derivatives

| 120-72-9 | Indole | 1H-Indole |

Saturated aliphatic acyclic branced-chain primary alcohols, aldehydes and acids

| 106-21-8 | 3,7-Dimethyl-1-octanol | 1-Octanol, 3,7-dimethyl- |

Saturated aliphatic acyclic secondary alcohols, ketones

| 111-13-7 | 2-Octanone | 2-Octanone |

Simple alphatic and aromatic sulfur compounds

| 39067-80-6 | Thiogeraniol | 2,6-Octadiene-1-thiol, 3,7-dimethyl-, (2E)- |

Others

| 23726-91-2 | (2E)-1-(2,6,6-Trimethyl-1-cyclohexen-1-yl)-2-buten-1-one | 2-Buten-1-one, 1-(2,6,6-trimethyl-1-cyclohexen-1-yl)-, (2E)- |
| 14901-07-6 | beta-Ionone | 3-Buten-2-one, 4-(2,6,6-trimethyl-1-cyclohexen-1-yl)- |
| 39255-32-8 | Ethyl 2-methylpentanoate | Pentanoic acid, 2-methyl-, ethyl ester |
| 1632-73-1 | Fenchyl alcohol | Bicyclo[2.2.1]heptan,2-ol, 1,3,3-trimethyl- |
| 122-78-1 | Phenylacetaldehyde | Benzeneacetaldehyde |
| 128-37-0 | Butylated hydroxytoluene | Phenol, 2,6-bis(1,1-dimethylethyl)-4-methyl- |
| 118-58-1 | Benzyl salicylate | Benzoic acid, 2-hydroxy-, phenylmethyl ester |
| 7452-79-1 | Ethyl 2-methylbutyrate | Butanoic acid, 2-methyl-, ethyl ester |
| 39255-32-8 | Ethyl 2-methylpentanoate | Pentanoic acid, 2-methyl-, ethyl ester |
| 128-37-0 | Butylated hydroxytoluene | Phenol, 2,6-bis(1,1-dimethylethyl)-4-methyl- |
| 8046-19-3 | Storax (Liquidambar spp.) | Storax, balsam |
| 38462-22-5 | p-Mentha-8-thiol-3-one | Cyclohexanone, 2-(1-mercapto-1-methylethyl)-5-methyl- |

Essential Oils (mixtures)

| 8016-20-4 | Grapefruit oil, expressed (*Citrus paradisi* Macf.) | Oils, grapefruit |
| 8022-15-9 | Lavandin oil (*Lavandula hybrida*) | Oils, lavandin |
| 8008-26-2 | Lime oil | Oils, lime |
| 8007-12-3 | Mace (*Myristica fragrans* Houtt.) | |
| 68606-94-0 | Orange oil distilled (*Citrus sinensis* (L.) Osbeck) | Oils, orange, sweet, terpene-free |
| 8008-57-9 | Orange oil terpeneless (*Citrus sinensis* (L.)) | Oils, orange, sweet |
| 8028-48-6 | Orange peel, sweet, extract (*Citrus sinensis* L.) | |
| 8008-31-9 | Mandarin oil, expressed | Oils, mandarin |
| 8008-56-8 | Lemon oil | Oils, lemon |
| 8023-89-0 | Elemi gum (*Canarium* spp.) | Oils, Manila elemi |
| 8014-17-3 | Petitgrain bigarade oil | Oils, petitgrain |
| 8000-34-8 | Clove bud oil (*Eugenia* spp.) | Oils, clove |
| 8015-90-5 | Celery seed (*Apium graveolens* L.) | Oils, celery |

TABLE 1-continued

Exemplary Fragrances

| CAS Number | Chemical Name | Other Name |
|---|---|---|
| 8016-26-0 | *Cistus* labdanum absolute | Oils, labdanum |
| 8000-34-8 | Clove bud oil (*Eugenia* spp.) | Oils, clove |
| 8008-52-4 | Coriander oil (*Coriandrum sativum* L.) | Oils, coriander |
| 8023-89-0 | Elemi gum (*Canarium* spp.) | Oils, Manila elemi |
| 8023-91-4 | Galbanum oil (*Ferula* spp.) | Oils, galbanum |
| 8007-08-7 | Ginger oil | |
| 8022-15-9 | Lavandin oil (*Lavandula hybrida*) | Oils, lavandin |
| 8008-56-8 | Lemon oil | Oils, lemon |
| 8007-02-1 | Lemongrass oil | |
| 68855-99-2 | *Litsea cubeba* oil | Oils, *Litsea cubeba* |
| 8008-31-9 | Mandarin oil, expressed | Oils, mandarin |
| 8016-36-2 | Olibanum absolute (*Boswellia* spp.) | Oils, olibanum |
| 68606-94-0 | Orange oil distilled (*Citrus sinensis* (L.) Osbeck) | Oils, orange, sweet, terpene-free |
| 8014-09-3 | Patchouly oil | |
| 8014-17-3 | Petitgrain bigarade oil | Oils, petitgrain |
| 8046-19-3 | Storax (*Liquidambar* spp.) | Storax, balsam |
| 8006-81-3 | Ylang-ylang oils | Oils, ylang-ylang |
| 8007-20-3 | Cedar leaf oil (*Thuja occidentalis* L.) | Oils, cedar leaf |
| 8008-79-5 | Spearmint oil | Oils, spearmint |

D. Solvents

In an embodiment, the composition may include very small concentrations of volatile solvents, e.g., that are soluble in water. Including a small amount of such volatile solvent may aid in providing enhanced filming and streaking (low residue) characteristics, and/or aid in solubilizing the fragrance. In an embodiment, other than water, the composition contains less than 0.5% of compounds with a vapor pressure over 0.1 mm Hg at 20° C. Many existing compositions rely on higher concentrations of such components to achieve desired sanitization targets, although such compositions exhibit less desirable aesthetics. Examples of such compounds include $C_1$ to $C_4$ alcohols, particularly $C_2$ to $C_4$ alcohols. Examples are listed in Table 2, below. Where included, such compounds other than water having a vapor pressure over 0.1 mm Hg at 20° C. may not be included at all, or may be included in an amount from 0.01% to less than 0.5%, 0.05% to 0.45%, 0.1% to 0.45%, or 0.25% to 0.45% by weight. Limiting concentration of such components to less than 0.5% by weight allows the composition to meet applicable EPA regulations, while also providing improved aesthetics and performance characteristics.

TABLE 2

Solvents

| Compound | Vapor Pressure mmHg @ 20° C. | Solubility in $H_2O$ (%) |
|---|---|---|
| Isopropyl alcohol | 33 | 100 |
| Ethanol | 43 | 100 |
| 2-methyl 1,3 propanediol | 0.021 (@25° C.) | 100 |
| 1,3 propanediol | 0.8 | 100 |
| 1,2, propylene glycol | 0.07 | 100 |

E. pH Adjusters

The present compositions may include one or more pH adjusters. In an embodiment, the pH adjuster may be an organic acid. The compositions typically do not require the inclusion of organic acids to achieve sanitization. Rather, if an organic acid is included at all, its purpose is for pH adjustment. In addition, many other compositions which include organic acids for sanitization also include a very low pH. According to an embodiment of the present disclosure, the present compositions include a pH that is typically in the range of about 3 to 12. In one embodiment the pH is at least 3, at least 4, more typically at least 5, at least 6, or from 6 to 8. The pH may be about 3 to 12, about 4 to 11, about 5 to 10, or about 6 to 9. Organic acids are organic compounds with acidic groups. The most common organic acids include but are not limited to, carboxylic acids and sulfonic acids. Organic acids are typically weak acids that usually do not completely dissociate in water. Another acid that may be suitable for use as a pH adjuster is phosphoric acid.

Exemplary organic acid pH adjusters include 2-hydroxycarboxylic acids or a mixture of 2-hydroxycarboxylic acids. Examples of 2-hydroxycarboxylic acids include, but are not limited to, tartaric acid, citric acid, malic acid, mandelic acid, oxalic acid, glycolic acid, and lactic acid. Citric acid, lactic acid, or mixtures thereof may be particularly useful, as they may also exhibit an antimicrobial effect, in addition to that provided by the quaternary amine. 2-Hydroxycarboxylic acids also include polymeric forms of 2-hydroxycarboxylic acid, such as polylactic acid. Another exemplary organic acid is acetic acid. Because the compositions do not require significant amounts of organic acid for sanitization efficacy, but merely for pH adjustment, the concentration of any included organic acid or other pH adjuster may be less than 2%, less than 1%, less than 0.5%, less than 0.2%, or less than 0.1%, by weight. Where present, an organic acid or other pH adjuster may be present in an amount of at least 0.001%, 0.01%, or 0.02% by weight (e.g., from 0.01 to 0.1% by weight).

Other exemplary pH adjusting agents may include, but are not limited to, mineral acids, alkali metal and alkaline earth salts of silicate, metasilicate, polysilicate, borate, hydroxide, carbonate, carbamate, phosphate, polyphosphate, pyrophosphates, triphosphates, tetraphosphates, ammonia, hydroxide, monoethanolamine, monopropanolamine, diethanolamine, dipropanolamine, triethanolamine, 2-amino-2-methylpropanol, and combinations thereof. Other pH or buffering agents include amino acids such as lysine or lower alcohol amines like mono-, di-, and tri-ethanolamine, tri(hydroxyl-methyl)

amino methane (TRIS), 2-amino-2-ethyl-1,3-propanediol, 2-amino-2-methyl-propanol, 2-amino-2-methyl-1,3-propanol, disodium glutamate, N-methyl diethanol-amide, 2-dimethylamino-2-methylpropanol (DMAMP), 1,3-bis (methyl-amine)cyclo-hexane, 1,3-diamino-propanol N,N'-tetra-methyl-1,3-diamino-2-propanol, N,N-bis(2-hydroxyethyl)glycine (bicine), N-tris(hydroxymethyl) methyl glycine (tricine), Other exemplary pH adjusting agents include ammonium carbamate, ammonia, alkali metal carbonates (e.g., sodium carbonate), alkali metal phosphates (e.g., sodium polyphosphate), alkali or alkaline earth hydroxides (e.g., sodium or potassium hydroxide). Mixtures of any suitable pH adjusting agents may also be employed. Additional buffers or pH adjusting agents are disclosed in WO 95/07971, which is incorporated herein by reference.

F. Optional Adjuncts

In a further aspect of the present invention, the cleaning composition includes and/or is used in combination with one or more adjuncts. The adjuncts include, but are not limited to, buffers, builders, solvents, stabilizers, defoamers, thickeners, hydrotropes, pH adjusters, anti-microbial compounds, and preservatives. Other optional adjuncts include but are not limited to, waxes, dyes and/or colorants, solubilizing materials, humectants, and lotions and/or mineral oils.

In an embodiment, the composition may not include various components that are typically included in other sanitizing compositions. For example, the composition may be void of biguanides (e.g., polybiguanides) (typically included in other compositions to achieve sanitization efficacy), relatively high levels of organic acids (typically included in other compositions to achieve sanitization, and/ or to lower pH to below 4, or below 3), relatively high levels of volatile organic compounds, such as the $C_1$-$C_4$ lower alcohols (typically included in other compositions to achieve sanitization). While very low levels of such components may be included in some embodiments, in an embodiment, the concentration of any such compounds with a vapor pressure over 0.1 mm Hg at 20° C. is less than 0.5% by weight.

Examples of such biguanides that are not included within at least some embodiments of the present compositions include chlorhexidine (1,1'-hexamethylene bis(5-(p-chlorophenyl)biguanide)). Other examples of biguanides that are often employed to achieve sanitizing efficacy are disclosed in U.S. Pat. No. 7,414,017 to Kong, herein incorporated by reference.

In some embodiments, various other components included in other sanitizing compositions are not included. Examples of such components that may not be included, in at least some compositions according to the present disclosure, include glycerol, glycerin (e.g., often included to solubilize one or more components), glycol ethers (e.g., often included with alcohols as solvents and/or solubilizers), and fatty acids.

Applicant's own earlier patents and/or publications including U.S. Pat. Nos. 7,396,808; 7,414,017; 7,511,006; and 2010/0330139 are herein incorporated by reference in their entirety. The present compositions may be void of any particular components described therein, other than those described as included within examples of the present compositions (e.g., water, a quaternary amine, a blend of two non-ionic surfactants, a fragrance, a C1-C4 lower alcohol, and a pH adjuster).

IV. Substrates

The sanitizing composition may be impregnated in, or otherwise provided with a cleaning substrate. A wide variety of materials can be used as the cleaning substrate. The substrate should have sufficient wet strength, abrasivity, loft and porosity. Examples of suitable substrates include, nonwoven substrates, woven substrates, hydroentangled substrates, foams and sponges. In an embodiment, the substrate may be in the form of a wipe. Any of these substrates may be water-insoluble, water-dispersible, or water-soluble. In one embodiment, the wipe weight is between 1 and 300 gsm, 1 and 200 gsm, 1 and 100 gsm, 10 and 100 gsm, 25 and 75 gsm, 30 and 60 gsm and 40 and 50 gsm. The thickness of the nonwoven substrate material is about 0.1 to about 1.0 mm, or about 0.2 to about 0.8 mm, 0.4 to about 0.6 mm.

In an embodiment, the composition is loaded onto the substrate such that there is at least a 2:1 loading ratio of sanitizing composition to substrate material by weight. The loading ratio may be anywhere in the range of 2:1 to about 11:1, preferably about 3:1 to about 5:1. The absorption capacity of the substrate may be at least 5 g/g, or at least 8 g/g or at least 10 g/g.

In one embodiment, the cleaning pad of the present invention comprises a nonwoven substrate or web. The substrate is composed of nonwoven fibers or paper. The term nonwoven is to be defined according to the commonly known definition provided by the "Nonwoven Fabrics Handbook" published by the Association of the Nonwoven Fabric Industry. A paper substrate is defined by EDANA (note 1 of ISO 9092-EN 29092) as a substrate comprising more than 50% by mass of its fibrous content made up of fibers (excluding chemically digested vegetable fibers) with a length to diameter ratio of greater than 300, and more preferably also has density of less than 0.040 $g/cm^3$. In one embodiment, the nonwoven substrate does not include woven fabric or cloth or sponge. In another embodiment of the invention, the nonwoven substrate material may include foam or sponge layers or foam or sponge particulate matter integrated into the nonwoven substrate material.

The substrate can be partially or fully permeable to water. The substrate can be flexible and the substrate can be resilient, meaning that once applied external pressure has been removed the substrate regains its original shape. In one embodiment the substrate has a machine direction tensile strength of at least 10 N/5 cm, or at least 20 N/5 cm, or at least 50 N/5 cm. The cross direction tensile strength may be at least 5 N/5 cm, at least 7 N/5 cm, or at least 10 N/5 cm.

Methods of making nonwovens are well known in the art. Generally, these nonwovens can be made by air-laying, water-laying, meltblowing, coforming, spunbonding, or carding processes in which the fibers or filaments are first cut to desired lengths from long strands, passed into a water or air stream, and then deposited onto a screen through which the fiber-laden air or water is passed. The air-laying process is described in U.S. Pat. Pub. No. 2003/0036741 to Abba and U.S. Pat. Pub. No. 2003/0118825 to Melius, both of which are herein incorporated by reference in their entirety. The resulting layer, regardless of its method of production or composition, is then subjected to at least one of several types of bonding operations to anchor the individual fibers together to form a self-sustaining substrate. The nonwoven substrate can be prepared by a variety of processes including, but not limited to, air-entanglement, hydroentanglement, thermal bonding, and combinations of these processes.

The substrate material may be patterned by a variety of different processes, including but not limited to, embossing, calendaring, tufting, crimping, and any other suitable processes to provide texture to the nonwoven substrate. Additionally, the first layer and the second layer, as well as additional layers, when present, can be bonded to one another in order to maintain the integrity of the article. The layers can be heat spot bonded together or using heat generated by ultrasonic sound waves. The bonding may be arranged such that geometric shapes and patterns, e.g. diamonds, circles, squares, etc. are created on the exterior surfaces of the layers and the resulting article. The layers may be hydroentangled together to form integrated layers or material.

The substrates can be provided dry, pre-moistened, or impregnated with sanitizing composition, but dry-to-the-touch. In one aspect, dry substrates can be provided with dry or substantially dry cleaning and sanitizing agents (e.g., the various components disclosed in the compositions herein, without the water) coated on or in the multicomponent multilobal fiber layer. In addition, the cleaning substrates can be provided in a pre-moistened and/or saturated condition. The wet sanitizing substrates can be maintained over time in a sealable container such as, for example, within a bucket with an attachable lid, sealable plastic pouches or bags, canisters, jars, tubs and so forth. Desirably the wet, stacked sanitizing substrates may be maintained in a resealable container. The use of a resealable container is particularly desirable when using aqueous liquid compositions since substantial amounts of liquid can evaporate while using the first substrates thereby leaving the remaining substrates with little or no liquid. Exemplary resealable containers and dispensers include, but are not limited to, those described in U.S. Pat. No. 4,171,047 to Doyle et al., U.S. Pat. No. 4,353,480 to McFadyen, U.S. Pat. No. 4,778,048 to Kaspar et al., U.S. Pat. No. 4,741,944 to Jackson et al., U.S. Pat. No. 5,595,786 to McBride et al. The entire contents of each of the aforesaid references are incorporated herein by reference. The substrates can be incorporated or oriented in the container as desired and/or folded as desired in order to improve ease of use or removal as is known in the art. The cleaning substrates of the present invention can be provided in a kit form, wherein a plurality of cleaning substrates and a cleaning tool are provided in a single package.

The substrate can include both natural and synthetic fibers. The substrate can also include water-soluble fibers or water-dispersible fibers, from polymers described herein. The substrate can be composed of suitable unmodified and/or modified natural fibers including cotton, Esparto grass, bagasse, hemp, flax, silk, wool, wood pulp, chemically modified wood pulp, jute, ethyl cellulose, and/or cellulose acetate. The modified natural fibers may be selected from the group consisting of: mercerized cotton, viscose rayon, cuprammonium rayon, lyocell rayon, fortisan rayon, and any combinations thereof. In another embodiment of the invention the natural unmodified fibers are cellulosic pulp fibers. Various pulp fibers can be utilized including, but not limited to, thermomechanical pulp fibers, chemi-thermomechanical pulp fibers, chemi-mechanical pulp fibers, refiner mechanical pulp fibers, stone groundwood pulp fibers, peroxide mechanical pulp fibers and so forth. In an embodiment, the substrate comprises only natural modified and/or unmodified cellulose fibers.

Suitable synthetic fibers can comprise fibers of one, or more, of polyvinyl chloride, polyvinyl fluoride, polytetrafluoroethylene, polyvinylidene chloride, polyacrylics such as ORLON®, polyvinyl acetate, polyethylvinyl acetate, non-soluble or soluble polyvinyl alcohol, polyolefins such as polyethylene (e.g., PULPEX®) and polypropylene, polyamides such as nylon, polyesters such as DACRON®, or KODEL®, polyurethanes, polystyrenes, and the like, including fibers comprising polymers containing more than one monomer. In an embodiment the synthetic fibers are limited to less than 10% of the nonwoven material, less than 5% of the nonwoven material, or less than 1% of the nonwoven material.

The substrate may be a multilayer laminate and may be formed by a number of different techniques including but not limited to using adhesive, needle punching, ultrasonic bonding, thermal calendering and through-air bonding. Such a multilayer laminate may be an embodiment wherein some of the layers are spunbond and some meltblown such as a spunbond/meltblown/spunbond (SMS) laminates as disclosed in U.S. Pat. No. 4,041,203 to Brock et al. and U.S. Pat. No. 5,169,706 to Collier, et al., each hereby incorporated by reference. The SMS laminate may be made by sequentially depositing onto a moving conveyor belt or forming wire first a spunbond web layer, then a meltblown web layer and last another spunbond layer and then bonding the laminate in a manner described above. Alternatively, the three web layers may be made individually, collected in rolls and combined in a separate bonding step.

The substrate may also contain superabsorbent materials. A wide variety of high absorbency materials (also known as superabsorbent materials) are known to those skilled in the art. See, for example, U.S. Pat. No. 4,076,663 to Masuda et al, U.S. Pat. No. 4,286,082 to Tsubakimoto et al., U.S. Pat. No. 4,062,817 to Westerman, and U.S. Pat. No. 4,340,706 to Obayashi et al. The absorbent capacity of such high-absorbency materials is generally many times greater than the absorbent capacity of fibrous materials. For example, a fibrous matrix of wood pulp fluff can absorb about 7-9 grams of a liquid, (such as 0.9 weight percent saline) per gram of wood pulp fluff, while the high-absorbency materials can absorb at least about 15, preferably at least about 20, and often at least about 25 grams of liquid, such as 0.9 weight percent saline, per gram of the high-absorbency material. U.S. Pat. No. 5,601,542, issued to Melius et al., discloses an absorbent article in which superabsorbent material is contained in layers of discrete pouches. Alternately, the superabsorbent material may be within one layer or dispersed throughout the substrate.

A. Cleaning Implements

In an embodiment of the invention, the composition may be used with a cleaning implement. In an embodiment of the invention, the cleaning implement may comprise a tool assembly disclosed in any of U.S. Pat. No. 7,386,910, entitled "Cleaning Tool with Gripping Assembly for a Disposable Scrubbing Head"; U.S. Pat. No. 7,065,825, entitled "Cleaning Tool with Gripping Assembly for a Disposable Scrubbing Head"; U.S. Pat. No. 6,953,299, entitled "Interchangeable Tool Heads"; U.S. application Ser. No. 10/817,606, entitled "Ergonomic Cleaning Pad", filed Apr. 1, 2004; and U.S. Pat. No. 7,065,838, entitled "Locking, Segmented Cleaning Implement Handle". Each of the foregoing are herein incorporated by reference in their entirety.

B. Wipes Dispenser Systems

Suitable wipes dispenser systems include both individually packaged sanitizing wipes and bulk packaged sanitizing wipes or other suitable sanitizing articles. The dispenser system may comprise a sealable container, which is substantially impervious to both liquid and/or gas. The term "container", refers to, but is not limited to, packets containing one or more individual wipes and bulk dispensers, such as canisters, tubs and jars, which may dispense one sanitizing wipe at a time, and further feature a suitable mechanism to reseal the bulk dispenser between uses to preserve the integrity of the sanitizing articles. One example is a cylindrical canister dispenser that houses a roll of individual wipes, separated by perforations to permit the tearing off of individual wipes for use. Such a dispenser is conveniently gripped by the user and held in position while the user removes a wipe. Suitable dispensers feature a resealable dispensing cap and orifice (See, e.g., Chong, U.S. Pat. No. 6,554,156, herein incorporated by reference) that dispenses individual wipes from a roll and retains the next wipe in a ready-to-dispense position, yet allows sealing of the dispensing cap to close the container against the environment when not in use. A further example, may include packaging individual wipes in a non-linked manner, in a dispenser permitting their removal one at a time.

concentration of a lower alcohol, and a fragrance as shown in Table 3 below. This example was designed to determine optimal concentrations of two surfactant types (an alcohol ethoxylate—EH9 and an alkyl polyglucoside—Glucopon® 215) for micro-efficacy and for phase stability (i.e., maintenance of a single phase). The fragrance in Examples 1-9 and 1-10 was varied to ensure fragrance component differences did not chance the micro-efficacy. Micro-efficacy testing was completed in suspension screening. Each example included 400 ppm of BTC® 1210 quaternary amine, and 0.45% isopropyl alcohol. The concentration of surfactants is noted in the table below. The balance of the composition was water. The fragrance concentration for each of the samples was 0.07 actives wt %.

TABLE 3

| Sample | Surfactant 1 Type | Surfactant 1 Level (wt %) | Surfactant 2 Type | Surfactant 2 Level (wt %) | Fragrance | pH | Total Surfactant (wt %) | *S. aureus* (Kill Rate - LR) % Reduction | *E. coli* (Kill Rate - LR) % Reduction |
|---|---|---|---|---|---|---|---|---|---|
| 1-1 | EH9 | 0.5 | — | — | 27 | 7.09 | 0.5 | 99.99999 | 99.99999 |
| 1-2 | EH9 | 0.67 | — | — | 27 | 6.63 | 0.67 | 99.99999 | 99.99999 |
| 1-3 | EH9 | 0.83 | — | — | 27 | 7.01 | 0.83 | 99.99999 | 99.99999 |
| 1-4 | EH9 | 1 | — | — | 27 | 7.23 | 1 | 99.99999 | 99.99999 |
| 1-5 | 215 | 0.3 | EH9 | 0.1 | 27 | 6.95 | 0.4 | 99.99999 | 99.99999 |
| 1-6 | 215 | 0.1 | EH9 | 0.25 | 27 | 6.94 | 0.35 | 99.99999 | 99.99999 |
| 1-7 | 215 | 0.5 | EH9 | 0.5 | 27 | 7.07 | 1 | 99.99999 | 99.99999 |
| 1-8 | 215 | 0.9 | EH9 | 0.1 | 27 | 6.68 | 1 | 99.99999 | 99.99999 |
| 1-9 | 215 | 0.1 | EH9 | 0.25 | Classic Lemon | 6.8 | 0.35 | 99.99999 | 99.99999 |
| 1-10 | 215 | 0.1 | EH9 | 0.25 | Fresh | 7.25 | 0.35 | 99.99999 | 99.99999 |

Wipe dispensers are convenient, and provide moistened sheets or wipes for a variety of uses. Wipes may be formulated for specific purposes, e.g., including, but not limited to sanitizing personal care wipes, dishwashing wipes, hard surface sanitizing wipes (e.g., for countertops, high chairs, toys, etc.,), and any other area in which a flexible substrate having a sanitizing liquid treatment composition safe for cleaning food contact surfaces has application.

C. Directions for Use

In an embodiment, typical directions for use may include wiping the food contact surface with a fresh wipe to pre-clean surfaces of filth and heavy soil. One may repeat as necessary until surfaces are visibly clean. To sanitize, one may wipe with the product. Wiping may be sufficient for the treated surface to remain visibly wet for at least 30 seconds, 1 minute, 2 minutes, or 3 minutes. The surface may be allowed to air dry, no rinsing required. The composition may also be provided in a form other than within a wipe (e.g., as a liquid sprayed, squeezed, squirted, or pumped from a container). To sanitize with such a spray or other liquid, the liquid may be sprayed or otherwise applied until the food contact surface is thoroughly wetted. The surface may be allowed to stand wet for at least 30 seconds, 1 minute, 2 minutes, or 3 minutes. The surface may then be wiped. For heavily soiled surfaces, a pre-cleaning step as described above may be helpful.

V. Examples and Testing Data

Example 1

Exemplary aqueous compositions were prepared including one or more surfactants, a quaternary amine, a low All of the tested formulations exhibited at least a 5 log reduction in micro-efficacy testing. In batching, it was noted that a minimum of 0.15% EH9 alcohol ethoxylate surfactant was preferred for providing effective solubilizing of the fragrance. Improved stability was observed with at least 0.2% EH9 surfactant.

Testing was performed to evaluate the streaking/filming performance of two similar formulations, one of which included 0.2% EH9, and 0.2% Glucopon®215, and the other of which included 0.4% EH9, with no Glucopon® 215. Both formulations included 0.4% total surfactant by weight. The formulation including 0.2% EH9 and 0.2% Glucopon® 215 exhibited significantly less streaking and/or filming when applied to hard tile. By blending the two surfactants, e.g., an alcohol ethoxylate (the EH9) and the alkyl polyglucoside (the Glucopon® 215), the filming/streaking characteristics are surprisingly advantageous in that the composition provides low streaking/filming characteristics of the alkyl polyglucoside while still exhibiting the excellent solubility characteristics (i.e., to solubilize the fragrance) of the alcohol ethoxylate.

Example 2

Various compositions were prepared including both an alcohol ethoxylate—(e.g., EH9) and an alkyl polyglucoside (e.g., Glucopon® 215) to evaluate filming and streaking performance, cleaning efficacy, and micro-efficacy (i.e., ability to sanitize) of each. The compositions each included 400 ppm (by weight) of BTC® 1210 quaternary amine, 0.45 wt % by weight isopropyl alcohol, and 0.08 wt % fragrance. Citric acid was used to adjust the pH into a neutral zone. The amount of citric acid (50%) added ranged from 0.02 wt % to 0.07 wt %. The balance of the compositions was water. The fragrance used in these compositions was a classic lemon fragrance with a concentration 0.07 actives wt %.

TABLE 4

| Sample | Surfactant 1 | | Surfactant 2 | | Total Surfactant (wt %) | pH |
|---|---|---|---|---|---|---|
| | Type | Level (wt %) | Type | Level (wt %) | | |
| 2-1 | EH9 | 0.2 | 215 | 0.55 | 0.75 | 6.91 |
| 2-2 | EH9 | 0.2 | 215 | 1.05 | 1.25 | 6.7 |
| 2-3 | EH9 | 0.2 | 215 | 1.55 | 1.75 | 6.96 |
| 2-4 | EH9 | 0.2 | 215 | 2.05 | 2.25 | 6.74 |
| 2-5 | EH9 | 0.8 | 215 | 0.55 | 1.35 | 6.66 |
| 2-6 | EH9 | 1.7 | 215 | 0.55 | 2.25 | 6.61 |

Various compositions were prepared similar to those in Table 4, but including increased concentration of quaternary amine (3000 ppm), with constant concentrations of alkyl polyglucoside (e.g., Glucopon® 215 or Glucopon® 420) and alcohol ethoxylate (e.g., EH9). Micelle competition was observed through micro-efficacy performance testing. Each of the compositions included 1.5 wt % alkyl polyglucoside (e.g., Glucopon® 215), 0.2% alcohol ethoxylate (e.g., EH9), 0.45 wt % by weight isopropyl alcohol, and 0.08 wt % fragrance. Citric acid was used to adjust the pH into a neutral zone. The amount of citric acid (50%) added ranged from 0.05 wt % to 0.06 wt %. The balance of the compositions was water.

TABLE 5

| Sample | Surfactant 1 | | Surfactant 2 | | Total Surfactant (wt %) | BTC® 1210 (wt %) | BTC® 835 (wt %) | pH |
|---|---|---|---|---|---|---|---|---|
| | Type | Level (wt %) | Type | Level (wt %) | | | | |
| 2-7 | EH9 | 0.2 | 215 | 1.5 | 1.75 | 0.3 | — | 7.01 |
| 2-8 | EH9 | 0.2 | 420 | 1.5 | 1.75 | 0.3 | — | 7 |
| 2-9 | EH9 | 0.2 | 215 | 1.5 | 1.75 | — | 0.3 | 7 |
| 2-10 | EH9 | 0.2 | 420 | 1.5 | 1.75 | — | 0.3 | 6.99 |

Examples 2-1, 2-3, 2-4, 2-5, and 2-6 were tested for cleaning performance using a controlled hard surface cleaning environment. Light load kitchen grease was used to evaluate the efficacy of each tested example. The results are shown in FIG. 1, which also shows results for comparative compositions Formula 409® and Clorox® Green Works®. FIG. 1 confirms that the compositions are capable of light duty cleaning by showing over 75% soil removal by each tested example by cycle 6. While the Formula 409® performed somewhat better than the tested samples, Formula 409® is a heavy duty cleaner, and not suitable for use in sanitizing food contact surfaces. The samples performed similarly to Clorox® Green Works®, which is also not specifically formulated for use in sanitizing food contact surfaces. While all of the tested examples performed similarly, the best examples for light duty cleaning efficacy were examples 2-3, 2-4, and 2-6, which included relatively higher surfactant concentrations.

The comparative compositions Formula 409® and Clorox® Green Works®, as well as examples 2-1 through 2-7 were evaluated for filming and streaking performance. The results are presented in Table 6.

TABLE 6

| Sample | Observations | Objective Ranking |
|---|---|---|
| Clorox® Green Works® | Clean - no filming or streaking | 1 |
| Formula 409® | Large streaks and droplet outlines | 9 |
| Sample 2-1 | Large droplet and significant streaking | 5 |
| Sample 2-2 | Minimal droplets, medium streaking | 4 |
| Sample 2-3 | No droplets - light streaking | 3 |
| Sample 2-4 | Very light streaking | 2 |
| Sample 2-5 | Medium-heavy streaking | 6 |
| Sample 2-6 | Heavy streaking | 7 |
| Sample 2-7 | Heavy streaking | 8 |

Filming and streaking was less evident in samples with higher amounts of alkyl polyglucoside (e.g., Glucopon®), and lower amounts of alcohol ethoxylate (e.g., EH9). As such, it may be beneficial to select a sufficient level of EH9 to solubilize the fragrance, with a relatively higher fraction of alkyl polyglucoside. In this embodiment of the invention, the ratio of alkyl polyglucoside to alcohol ethoxylate surfactants may be greater than 1:1. For example, Sample 2-2 had a ratio of 5.25:1, sample 2-3 had a ratio of 7.75:1, and sample 2-4 had a ratio of 10.25:1.

Various of the exemplary compositions were tested for their micro-efficacy (i.e., their ability to kill bacteria) against *S. aureus* using test method AOAC 960.09. Contact time was 30 seconds. Neutralizer employed was D/E broth. Results were as detailed in Table 7 below.

TABLE 7

| Sample | Control CFU | Surviving CFU | Log Reduction |
|---|---|---|---|
| Sample 2-3 | $3.2 \times 10^9$ | $6.35 \times 10^5$ | 3.7 |
| Sample 2-4 | $3.2 \times 10^9$ | $5.4 \times 10^7$ | 2.93 |
| Sample 2-7 | $3.2 \times 10^9$ | 0 | 5.5 (limit of detection) |
| Sample 2-9 | $3.2 \times 10^9$ | 0 | 5.5 (limit of detection) |
| Control | $3.2 \times 10^9$ | 0 | 5.5 (limit of detection) |

The results may indicate a "cliff" where the alkyl polyglucoside (e.g., Glucopon®) may be interfering with the efficacy of the quaternary amine. Examples 2-3 and 2-4 had a Glucopon® 215 concentration of 1.55 wt % and 2.05 wt %, respectively. The control had a level of 0.8% of alkyl polyglucoside (e.g., Glucopon® 215).

In summary, the various testing shows that relatively higher amounts of alkyl polyglucoside surfactant within the composition provided better cleaning efficacy, with relatively lower streaking and filming. At the same time, alkyl polyglucosides (e.g., Glucopon® 215) appear to inhibit the micro performance of the quaternary amine at relatively higher levels. Thus, in an embodiment, to provide excellent low filming, low streaking, good cleaning performance, while providing a high log (e.g., at least log 5) bacterial reduction, the concentration of the alkyl polyglucoside may be from 0.8% to 1.55%. Alternatively, in some embodiments of the invention the composition may comprise only alcohol ethoxylate surfactant to provide a high log (e.g., at least log 5) bacterial reduction and good cleaning performance with slightly higher levels of residue (e.g. filming and streaking) than the blended surfactant composition, described above. For certain cleaning applications (e.g. low gloss surfaces, non-reflective surfaces, etc.) slightly higher levels of residue may be acceptable provided that cleaning performance and bacterial reduction are maintained or improved.

Example 3

Various compositions were prepared to evaluate fragrance solubility using various surfactants and surfactant concentrations. "Sunkissed Citrus" and "Koala" fragrances used in Clorox® disinfecting wipes were used as proxies because of the unavailability of actual fragrances at the time of the test. Even using proxy fragrances, the testing provided data on a surfactant's ability to solubilize a fragrance. Each aqueous composition example included 400 ppm of quaternary amine (BTC® 2125M or BTC® 1210), 0.4 wt % isopropyl alcohol, and 0.1 wt % fragrance, with the balance consisting of water, or consisting essentially of water. The results are summarized in the tables 8A-8F below.

TABLE 8A

Results after 24 hrs
2125M, Sunkissed Citrus
Surfactant Type and Concentration

| 0.15 wt % | 0.24 wt % | 0.33 wt % | 0.41 wt % | 0.5 wt % |
|---|---|---|---|---|
| EH6[1] | EH6[1] | EH6[1] | EH6[1] | EH6[1] |
| EH9[1] | EH9[1] | EH9[1] | EH9[3] | EH9[3] |
| XL70[1] | XL70[1] | XL70[1] | XL70[1] | XL70[1] |
| XL90[1] | XL90[1] | XL90[1] | XL90[1] | XL90[1] |

TABLE 8B

Results after 24 hrs
1210, Sunkissed Citrus
Surfactant Type and Concentration

| 0.15 wt % | 0.24 wt % | 0.33 wt % | 0.41 wt % | 0.5 wt % |
|---|---|---|---|---|
| EH6[1] | EH6[1] | EH6[1] | EH6[1] | EH6[1] |
| EH9[1] | EH9[1] | EH9[1] | EH9[3] | EH9[3] |
| XL70[1] | XL70[1] | XL70[1] | XL70[1] | XL70[1] |
| XL90[1] | XL90[1] | XL90[1] | XL90[1] | XL90[1] |

TABLE 8C

Results after 2 hours
2125M, Koala
Surfactant Type and Concentration

| 0.15 wt % | 0.24 wt % | 0.33 wt % | 0.41 wt % | 0.5 wt % |
|---|---|---|---|---|
| EH6[1] | EH6[1] | EH6[1] | EH6[2] | EH6[2] |
| EH9[1] | EH9[2] | EH9[3] | EH9[3] | EH9[3] |
| XL70[1] | XL70[1] | XL70[2] | XL70[3] | XL70[3] |
| XL90[1] | XL90[1] | XL90[1] | XL90[1] | XL90[2] |

TABLE 8D

Results after 2 hours
1210, Koala
Surfactant Type and Concentration

| 0.15 wt % | 0.24 wt % | 0.33 wt % | 0.41 wt % | 0.5 wt % |
|---|---|---|---|---|
| EH6[1] | EH6[1] | EH6[1] | EH6[1] | EH6[2] |
| EH9[1] | EH9[2] | EH9[3] | EH9[3] | EH9[3] |
| XL70[1] | XL70[2] | XL70[3] | XL70[3] | XL70[3] |
| XL90[1] | XL90[1] | XL90[1] | XL90[2] | XL90[2] |

TABLE 8E

Results after 72+ hours
2125M, Koala
Surfactant Type and Concentration

| 0.15 wt % | 0.24 wt % | 0.33 wt % | 0.41 wt % | 0.5 wt % |
|---|---|---|---|---|
| EH6[1] | EH6[1] | EH6[1] | EH6[1] | EH6[1] |
| EH9[1] | EH9[1] | EH9[3] | EH9[3] | EH9[3] |
| XL70[1] | XL70[1] | XL70[1] | XL70[3] | XL70[3] |
| XL90[1] | XL90[1] | XL90[1] | XL90[1] | XL90[1] |

TABLE 8F

Results after 72+ hours
1210, Koala
Surfactant Type and Concentration

| 0.15 wt % | 0.24 wt % | 0.33 wt % | 0.41 wt % | 0.5 wt % |
|---|---|---|---|---|
| EH6[1] | EH6[1] | EH6[1] | EH6[1] | EH6[1] |
| EH9[1] | EH9[1] | EH9[3] | EH9[3] | EH9[3] |
| XL70[1] | XL70[1] | XL70[3] | XL70[3] | XL70[3] |
| XL90[1] | XL90[1] | XL90[1] | XL90[1] | XL90[1] |

(1)—these compositions were cloudy.
(2)—these compositions were hazy.
(3)—these compositions were clear.

The results of Example 3 show that EH9 exhibited better solubilizing characteristics relative to a fragrance as compared to surfactants EH6, XL70, and XL90.

Example 4

Various compositions were prepared to evaluate micro-efficacy for various compositions at different pH values. Each composition included 400 ppm of a quaternary amine (BTC® 2125M or BTC® 1210), from 0.33 wt % to 0.5 wt % EH9 surfactant, 0.075 wt % fragrance ("Limon Classico Mod", from IFF, Inc.), and 0.45 wt % isopropyl alcohol. pH values were adjusted with citric acid and/or $Na_4EDTA$. The micro-efficacy results (e.g., against *S. aureus*) are shown in Table 9 below.

TABLE 9

| Sample | EH9 (wt %) | pH | Quat. Type | Log Reduction |
|---|---|---|---|---|
| Sample 4-1 | 0.42 | 6.50 | 1210 | 6 |
| Sample 4-2 | 0.33 | 10.00 | 2125M | 6 |
| Sample 4-3 | 0.42 | 3.00 | 1210 | 3.14 |
| Sample 4-4 | 0.42 | 6.50 | 2125M | 5 |
| Sample 4-5 | 0.5 | 10.00 | 1210 | 6 |
| Sample 4-6 | 0.42 | 10.00 | 1210 | 6 |
| Sample 4-7 | 0.33 | 3.00 | 1210 | 4.05 |
| Sample 4-8 | 0.42 | 6.50 | 2125M | 5 |
| Sample 4-9 | 0.42 | 6.50 | 1210 | 6 |
| Sample 4-10 | 0.42 | 6.50 | 1210 | 6 |

TABLE 9-continued

| Sample | EH9 (wt %) | pH | Quat. Type | Log Reduction |
|---|---|---|---|---|
| Sample 4-11 | 0.33 | 6.50 | 2125M | 6 |
| Sample 4-12 | 0.50 | 10.00 | 2125M | 6 |
| Sample 4-13 | 0.50 | 6.50 | 1210 | 6 |
| Sample 4-14 | 0.50 | 3.00 | 2125M | 4.05 |
| Sample 4-15 | 0.33 | 10.00 | 1210 | 6 |
| Sample 4-16 | 0.42 | 6.50 | 2125M | 5 |
| Sample 4-17 | 0.42 | 6.50 | 1210 | 6 |
| Sample 4-18 | 0.33 | 3.00 | 2125M | 4.05 |
| Sample 4-19 | 0.50 | 6.50 | 2125M | 4.22 |
| Sample 4-20 | 0.33 | 6.50 | 1210 | 6 |
| Sample 4-21 | 0.42 | 3.00 | 2125M | 4.05 |

TABLE 9-continued

| Sample | EH9 (wt %) | pH | Quat. Type | Log Reduction |
|---|---|---|---|---|
| Sample 4-22 | 0.42 | 6.50 | 2125M | 5 |
| Sample 4-23 | 0.42 | 6.50 | 2125M | N/A |
| Sample 4-24 | 0.50 | 3.00 | 1210 | 4.05 |
| Sample 4-25 | 0.42 | 10.00 | 1210 | 6 |
| Sample 4-26 | 0.42 | 6.50 | 1210 | N/A |

The results showed that BTU) 1210 was less susceptible to interactions with the EH9 surfactant than BTC® 2125M, providing better micro-efficacy results. The results also showed that relatively higher levels of EH9 surfactant can affect the efficacy of the quaternary amine, and that relatively lower pH values (e.g., a pH of 3, or less than 3) also negatively affected the efficacy of the quaternary amine. For these reasons, it may be beneficial to provide a pH value of greater than 3, e.g., from 6 to 8.

In conducting filming and streaking testing of these examples, it was found that the EH9 surfactant exhibited relatively high streaking and filming (i.e., residue) when used alone. As described herein, by using an alkyl polyglucoside with the alcohol ethoxylate (e.g., EH9), excellent low residue performance can be obtained. This is particularly surprising that the streaking and filming of the alcohol ethoxylate may be overcome, not by decreasing the concentration of the alcohol ethoxylate, but by adding a alkylpolyglucoside surfactant (i.e., actually increasing the surfactant level).

Example 5

As a follow up to Example 4, various compositions were prepared and subjected to micro-efficacy testing to evaluate whether $Na_4EDTA$ added as a pH adjuster to the higher pH compositions was contributing to micro-efficacy results, or if all results were attributable to the quaternary amine alone. In order to make this evaluation, pH was adjusted to higher pH values using NaOH, as compared to using $Na_4EDTA$ as a pH adjuster.

TABLE 10

| Sample | pH | Surfactant Type | Surf. Concentration (wt %) | EDTA (g) | Citric Acid (50%) | % Reduction (S. aureus) | % Reduction (E. coli) |
|---|---|---|---|---|---|---|---|
| Sample 5-1 | 10 | EH9 | 0.33 | 0.3 | — | >99.999 | >99.999 |
| Sample 5-2 | 10 | EH9 | 0.33 | 1 drp NaOH | — | >99.999 | >99.999 |
| Sample 5-3 | 6.5 | EH9 | 0.33 | 0.3 | 1 drp (0.05 mL) | >99.999 | >99.999 |
| Sample 5-4 | 6.5 | EH9 | 0.33 | — | — | >99.999 | >99.999 |
| Sample 5-5 | 6.5 | EH9 | 1 | 0.47 | 1 drp (0.05 mL) | 99.987 | >99.999 |
| Sample 5-6 | 10 | EH9 | 1 | 0.3 | — | >99.999 | 99.992 |
| Sample 5-7 | 6.5 | 215 | 0.33 | — | 1 drp (0.05 mL) | >99.999 | >99.999 |
| Sample 5-8 | 10 | 215 | 0.33 | — | — | >99.999 | 99.992 |
| Sample 5-9 | 6.5 | 215 | 1 | — | 1 drp (0.05 mL) | >99.999 | >99.999 |
| Sample 5-10 | 10 | 215 | 1 | — | — | >99.999 | >99.999 |
| Sample 5-11 | 6.5 | EH9 | 0.33 | — | 1 drp (0.05 mL) | 99.987 | 99.992 |
| Sample 5-12 | 10 | EH9 | 0.33 | 0.3 | 1 drp (0.05 mL) | 99.987 | 99.992 |

As with all micro-efficacy testing, the study of Example 5 was done with the compositions in suspension. The results of the testing are consistent with those of the previous examples, showing that EH9 can have an adverse effect on micro-efficacy of the quaternary amine. Samples 5-11 and 5-12 do not contain any quaternary amine. Samples 5-11 and 5-12 are the negative controls to show that the quat is necessary to achieve the requisite % Reduction in S. aureus and E. coli that is achieved by samples 5-1 to 5-10. For this reason, in an embodiment, the alcohol ethoxylate may be maintained at no more than 1%, or no more than 0.8%, or no more than 0.6%, or no more than 0.4% by weight. The data also show that relatively higher levels of the alkyl polyglucoside (e.g., Glucopon® 215) may increase micro-efficacy. The data was inconclusive with regards to the roll of pH in micro-efficacy. It shows log 5 reduction or better results at high pH and generally neutral pH values, achieved with addition of various pH adjusters.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

The invention claimed is:

1. A fragranced sanitizing liquid composition for sanitizing surfaces which contact food, the composition consisting of:
   (a) about 100 ppm to 400 ppm of a quaternary amine comprising: a benzalkonium chloride;
   (b) about 0.1 to 4% by weight of one or more non-ionic surfactants selected from the group consisting of: $C_8$-$C_{10}$ alkyl polyglucosides, alkyl polyethylene glycol ethers, alcohol ethoxylates, and any mixtures or combinations thereof, wherein the at least one non-ionic surfactant includes an alcohol ethoxylate surfactant, the alcohol ethoxylate surfactant being present in an amount of no more than 0.4% by weight;
   (c) a fragrance wherein at least 90% by weight of the fragrance comprises fragrance components that meet Class I qualifications of the Cramer classification system, wherein the fragrance provides a scent to the composition;
   (d) at least 90% by weight of water; and
   (e) a $C_1$-$C_4$ alcohol solvent;
   (f) optionally, a pH adjuster at less than 0.1% by weight;
   wherein the composition has a pH from 6.5 to 10;
   wherein the fragranced sanitizing liquid composition only contains components that are generally recognized as safe for use in sanitizing food contact surfaces with a no rinse application;
   wherein the sanitizing liquid composition provides at least a 3 log reduction in a bacterial population within 1 minute.

2. The composition of claim 1, wherein the composition is void of polybiguanides.

3. The composition of claim 1, wherein the composition includes less than 0.5% by weight of volatile components other than water with a vapor pressure over 0.1 mm Hg at 20° C.

4. The composition of claim 1, wherein the nonionic surfactant is a $C_8$-$C_{10}$ alkyl polyglucoside.

5. The composition of claim 1, wherein the $C_1$-$C_4$ alcohol comprises isopropyl alcohol at a level of 0.01 to 0.50% by weight.

6. The composition of claim 1, wherein the one or more non-ionic surfactants collectively comprise no more than 2% by weight of the composition.

7. The composition of claim 1, wherein the non-ionic surfactant is an alcohol ethoxylate, present in an amount from 0.2% to 0.4% by weight.

8. The composition of claim 1, wherein the composition includes both a $C_8$-$C_{10}$ alkyl polyglucoside surfactant and an alcohol ethoxylate surfactant.

9. The composition of claim 1, wherein the composition has a pH from 6.5 to 8.

10. The composition of claim 1, wherein the quaternary amine is included in a concentration of about 200 ppm to 400 ppm.

11. A fragranced sanitizing liquid composition for sanitizing surfaces which contact food, the composition consisting of:
    (a) about 100 ppm to 400 ppm of a quaternary amine comprising: a benzalkonium chloride;
    (b) a blend of an alcohol ethoxylate surfactant and a $C_8$-$C_{10}$ alkyl polyglucoside surfactant wherein the weight ratio of the $C_8$-$C_{10}$ alkyl polyglucoside to the alcohol ethoxylate is from 1:1 to 10:1, wherein the composition does not include a glycol ether;
    (c) a fragrance wherein at least 90% by weight of the fragrance comprises fragrance components that meet Class I qualifications of the Cramer classification system, wherein the fragrance provides a scent to the composition;
    (d) at least 90% by weight of water;
    (e) about 0.01% to 0.5% by weight of a $C_1$-$C_4$ alcohol; and
    (f) optionally, one or more adjuncts selected from the group consisting of: buffers, pH adjusters, and preservatives; and
    (g) wherein the fragranced sanitizing liquid composition only contains components that are generally recognized as safe for use in sanitizing food contact surfaces with a no rinse application;
    (h) wherein the composition is void of polybiguanides, and includes less than 0.5% of volatile components other than water with a vapor pressure over 0.1 mm Hg at 20° C.; and
    (i) wherein the composition has a pH from 6.5 to 10;
    wherein the sanitizing liquid composition provides at least a 3 log reduction in a bacterial population within 1 minute.

12. The composition of claim 11, wherein a weight ratio of the $C_8$-$C_{10}$ alkyl polyglucoside to the alcohol ethoxylate is greater than 1:1.

13. The composition of claim 11, wherein the composition has a pH from 6.5 to 8.

14. The composition of claim 11, wherein the quaternary amine is included in a concentration of about 200 ppm to 400 ppm.

15. A fragranced sanitizing liquid composition for sanitizing surfaces which contact food, the composition consisting of:
    (a) about 400 ppm of a quaternary amine comprising: a benzalkonium chloride;
    (b) two or more non-ionic surfactants selected from the group consisting of: $C_8$-$C_{10}$ alkyl polyglucosides, alkyl polyethylene glycol ethers, alcohol ethoxylates, and any mixtures or combinations thereof, wherein at least one of the non-ionic surfactants is an alcohol ethoxylate, the alcohol ethoxylate being present in an amount of no more than 0.4% by weight;
    (c) a fragrance wherein at least 90% by weight of the fragrance comprises fragrance components that meet Class I qualifications of the Cramer classification system, wherein the fragrance provides a scent to the composition;
    (d) at least 98% by weight of water; and
    (e) a $C_1$-$C_4$ alcohol solvent;
    (f) optionally, one or more adjuncts selected from the group consisting of: buffers, pH adjusters, and preservatives, wherein any pH adjuster is present at less than 0.1% by weight;
    wherein the composition has a pH from 6.5 to 10;
    wherein the composition includes less than 0.5% by weight of volatile components other than water with a vapor pressure over 0.1 mm Hg at 20° C.;
    wherein the fragranced sanitizing liquid composition only contains components that are generally recognized as safe for use in sanitizing food contact surfaces with a no rinse application;
    wherein the sanitizing liquid composition provides at least a 3 log reduction in a bacterial population within 1 minute.

* * * * *